US006245883B1

(12) United States Patent
Heerze et al.

(10) Patent No.: US 6,245,883 B1
(45) Date of Patent: *Jun. 12, 2001

(54) ANTI-FLAMMATORY CARBOHYDRATE BINDING-PEPTIDES

(75) Inventors: Louis D. Heerze; Glen D. Armstrong; Richard Smith, all of Edmonton (CA)

(73) Assignee: Alberta Research Council, Alberta (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/149,860

(22) Filed: Sep. 9, 1998

Related U.S. Application Data

(63) Continuation of application No. 08/390,509, filed on Feb. 17, 1995, now Pat. No. 5,833,990, which is a continuation of application No. 07/995,503, filed on Dec. 21, 1992, now Pat. No. 5,453,272, which is a continuation-in-part of application No. 07/956,043, filed on Oct. 2, 1992, now abandoned.

(51) Int. Cl.[7] .................... A61K 38/00; A61K 39/00; A61K 39/10; C07K 2/00; C07K 7/00

(52) U.S. Cl. .................... 530/300; 530/350; 530/324; 530/326; 530/327; 530/329; 530/868; 424/184.1; 424/185.1; 424/240.1; 424/282.1; 424/275.1; 424/190.1; 514/2; 514/885

(58) Field of Search .................... 530/350, 326, 530/300, 327, 868, 324, 329; 424/184.1, 185.1, 240.1, 282.1, 275.1, 190.1; 514/885, 2

(56) References Cited

U.S. PATENT DOCUMENTS

| | | |
|---|---|---|
| 4,742,046 | 5/1988 | Bliah . |
| 5,079,353 | 1/1992 | Ratcliffe et al. . |
| 5,081,034 | 1/1992 | Bevilacqua et al. . |
| 5,154,923 | 10/1992 | Van Eden et al. . |
| 5,157,023 | 10/1992 | Lipton . |
| 5,198,424 | 3/1993 | McEver . |
| 5,433,945 | * 7/1995 | Klein et al. . |
| 5,440,015 | 8/1995 | Macher et al. . |
| 5,453,272 | 9/1995 | Heerze et al. . |
| 5,496,934 | * 3/1996 | Shoseyov et al. . |
| 5,550,155 | 8/1996 | Kashem et al. . |
| 5,670,623 | * 9/1997 | Shoseyov et al. . |
| 5,719,044 | * 2/1998 | Shoseyov et al. . |
| 5,736,143 | * 4/1998 | Heerze et al. . |
| 5,747,040 | * 5/1998 | Heerze et al. . |
| 5,833,990 | * 11/1998 | Heerze et al. . |
| 5,837,814 | * 11/1998 | Shoseyov et al. . |
| 5,856,122 | * 1/1999 | Read et al. . |
| 5,858,965 | * 1/1999 | Ben-Nun . |
| 5,965,385 | * 10/1999 | Read et al. . |
| 5,977,304 | * 11/1999 | Read et al. . |
| 6,018,022 | * 1/2000 | Read et al. . |
| 6,168,928 | * 1/2001 | Read et al. . |

FOREIGN PATENT DOCUMENTS

| | | |
|---|---|---|
| 45665/85 | 7/1985 | (AU) . |
| 33182/89 | 4/1989 | (AU) . |
| 0 173 092 | 3/1986 | (EP) . |
| 0 232 229 | 8/1987 | (EP) . |
| 0 338 566 | 10/1989 | (EP) . |
| WO91/07977 | 6/1991 | (WO) . |
| WO91/08231 | 6/1991 | (WO) . |
| WO91/08294 | 6/1991 | (WO) . |
| WO91/19501 | 12/1991 | (WO) . |
| WO91/19502 | 12/1991 | (WO) . |
| WO92/01718 | 2/1992 | (WO) . |
| WO92/02527 | 2/1992 | (WO) . |
| WO92/07572 | 5/1992 | (WO) . |
| WO92/09293 | 6/1992 | (WO) . |
| WO92/16612 | 10/1992 | (WO) . |
| WO92/19646 | 11/1992 | (WO) . |
| WO93/18782 | 9/1993 | (WO) . |
| WO94/07517 | 4/1994 | (WO) . |
| WO96/17620 | 6/1996 | (WO) . |

OTHER PUBLICATIONS

Cummings et al, Biochemistry, 37:1789–1799, 1998.*
Wang et al, Glycobiology, 2/5:499, 1992.*
Locht et al, Science, 232:1256–1264, 1986.*
Hazes et al, J. Mol. Biol., 258:661–671, 1996.*
Nicosia et al, PNAS, 83:4631–4635, 1986.*
Arico et al, J. Bacteriology, 169/6:2847–2853, 1987.*
Heerze et al, Glycobiology, 5/4:427–433, 1995.*
Albelda, et al., In "Integrins and other cell adhesion molecules", *The FASEB Journal*, 4:2868–2880 (1990).
Aplin, et al., "Complex Carbohydrates of the Extracellular Matrix Structures, Interactions and Biological Roles", *Biochem. Biophys. Acta*, 694:375–418 (1982).
Armstrong, et al., "Maintenance of Biological Activity of Pertussis Toxin Radioiodinated While Bound to Fetuin–Agarose", *Infect. Immun.*, 55:1294–1299 (1987).
Armstrong, et al., "Use of glycosyltransferases to Restore Pertussis Toxin Receptor Activity to Asialoagalactofetuin", *J. Biol. Chem.*, 263:8677–8684 (1988).
Barondes, "Developmentally Regulated Lectins", In *Cell Interactions and Development: Molecular Mechanisms* (Yamada, D.M., Ed.), pp. 185–202 (1983).

(List continued on next page.)

*Primary Examiner*—Nita Minnifield
(74) *Attorney, Agent, or Firm*—Burns, Doane, Swecker & Mathis, LLP

(57) ABSTRACT

The present invention is directed to lectin derived carbohydrate binding peptides or derivatives thereof useful for suppressing inflammatory responses, inducing tolerance to an antigen, and suppressing cell adhesion, e.g., involved in metastasis. In particular, peptides capable of binding terminally linked α-sialic acid(2–6)βGal- and/or α-sialic acid (2–3)βGal-groups on structures or molecules comprising such groups are provided. Pharmaceutical compositions containing such lectin derived carbohydrate binding peptides are also disclosed.

28 Claims, 3 Drawing Sheets

OTHER PUBLICATIONS

Bevilacqua, et al., "Endothelial–Leukocyte Adhesion Molecule—1 (ELAM–1): A Vascular Selectin That Regulates Inflammation". In *Cellular and Molecular Mechanisms of Inflammation*, vol. 2:1–13 (1991).

Bhavanandan, et al., The Interaction of Wheat Germ Agglutinin with Sialoglycoproteins *J. Biol. Chem.*, 254:4000–4008 (1979).

Brandley, et al., "Cell–Surface Carbohydrates in Cell Recognition and Response" *J. Leukocyte Biol.*, 40:97–111 (1986).

Brennan, et al., "Lectin–like binding of Pertussis Toxin to a 165–Kilodalton Chinese Hamster Ovary Cell Glycoprotein", *J. Biol. Chem.*, 263:4895–4899 (1988).

Bystrn, *Cancer & Metastasis Rev.*, 9:81–91 (1990).

Chou, et al., "Empirical Predictions of Protein Conformation", *Annu. Rev. Biochem.*, 47:251–276 (1978).

Coutinho, et al., "T Cell–Dependent B Cell Activation", *Immunol. Rev.*, 78:211–224 (1984).

Ekblom, et al., "The Extracellular Matrix and Kidney Differentiation", In *Membranes in Growth and Development*, Hoffmann, et al., Eds., pp. 429–442, (1982).

Frazier, et al., "Surface Components and Cell Recognition", *Annu. Rev. Biochem.*, 48:491–523 (1979).

Furukawa, et al., "Interaction of Sialoglycoproteins with Wheat Germ Agglutinin–Sepharose of Varying Ratio of Lectin to Sepharose", *J. Biol. Chem.*, 261:7755–7761 (1986).

Glaser, "From Cell Adhesion to Growth Control", *Mediator of Developmental Processes* (Substency, S. and Wessels, N.K., Eds.), pp. 79–97 (1980).

Hakomori, "Aberrant Glycosylation in Tumors and Tumor–Associated Carbohydrate Antigens", *Adv. Cancer Res.*, 52:257–331 (1989).

Heerze, et al., "Comparison of the Lectin–Like Activity of Pertussis Toxin with Two Plant Lectins That Have Differential Specificities for $\alpha(2-6)$ And $\alpha(2-3)$–Linked Sialic Acid", *Biochem. Biophys. Res. Comm.*, 172:1224–1229 (1990).

Heerze, et al., "Synthesis and Characterization of a Pertussis Toxin–Biotin Conjugate", *Biochem. Biophys. Res. Comm.*, 179:1464–1469 (1991).

Heerze, et al., "Investigation of the Lectin–like Binding Domains in Pertussis Toxin Using Synthetic Peptide Sequences," *J. Biol. Chem.*, 267:25810–35815 (1992).

Hogg, "Roll, roll, roll your leucocyte gently down the vein . . . ," *Immunology Today*, 13:113–115 (1992).

Hopp, et al., "Prediction of Protein Antigenic Determinants from Amino Acid Sequences", *Proc. Natl. Acad. Sci. U.S.A.*, 78:3824–3828 (1981).

Houghten, et al., *Vaccine*, 86:21–25 (1986).

Jacobson, "Beginnings of the Nervous System", *Developmental Neurobiology*, New York, Plenum Press, pp. 5–25, (1978).

Karlsson, "Animal Glycosphingolipids as Membrane Attachment Sites For Bacteria", *Annu. Rev. Biochem.*, 58:309–350 (1989).

Larsen, et al., "PADGEM–Dependent Adhesion of Platelets to Monocytes and Neutrophils is Mediated by a Lineage–Specific Carbohydrate LNF III (CD15)", *Cell*, 63:467–474 (1990).

Larsen, et al., "P–selectin and E–selectin", *J. Biol. Chem.*, 267:11104–11110 (1992).

Lowe, et al., "ELAM–1–Dependent Cell Adhesion to Vascular Endothelium Determined by a Transfected Human Fucosyltransferase cDNA", *Cell*, 63:475–484 (1990).

McEver, "Leukocyte Interactions Mediated by GMP–140", In *Cellular and Molecular Mechanisms of Inflammation*, vol.2:15–29 (1991).

Moore, G.J., *Trends in Pharmacological Sciences*, 15:124–129 (1994).

Morgan, et al., "Approaches to the Discovery of Non–Peptide Ligands for Peptide Receptors and Peptidases," In *Annual Reports in Med. Chem.*, 24:243–252 (1989).

Munoz, "Action of Pertussigen (Pertussis Toxin) on the Host Immune System", In *Patho. and Immunity in Pertussis*, p. 173–192 (1988).

Neuberger, A., "What Lectins and Carbohydrates are Made For?", *Biol. Cell*, 51 (Special Issue), pp. 113–114, 1984.

Nicolson, et al., "Preferential Organ Attachment and Invasion in vitro by B16 Melanoma Cells Selected for Differing Metastatic Colonization and Invasive Properties", *Invas. Metas.*, 5:144–158 (1985).

Nogimori, et al., "Structure–Function Relationship of Islet–Activating Protein Pertussis Toxin: Biological Activities of Hybrid Toxins Reconstituted from Native and Methylated Subunits", *Biochem.*, 25:1355–1363 (1986).

Olson, et al., *J. Medicinal Chem.*, 36(21):3039–3049 (1993).

Paulson, "Interactions of Animal Viruses with Cell Surface Receptors", In *The Receptors*, vol. II (Comm., P.M., Ed.), pp. 131–219 (1985).

Pearce–Pratt, et al., "Simple Calorimetric Cell—Cell Adhesion Assay Using Biotinylated Lymphocytes", *J. Imm. Methods*, 140:159–165 (1991).

Phillips, et al., "ELAM–1 Mediates Cell Adhesion by Recognition of a Carbohydrate Ligand Sialyl–Le$^{x}$", *Science*, vol. 250:1130–1132 (1990).

Protein Segenes on STN: Quick Reference Guide published by CAS, p. 2 (Apr. 1992).

Repine, "Scientific perspectives on adult respiratory distress syndrome", *The Lancet, Science & Practice*, 339:466–469 (1992).

Reuter, et al., Schauer, Ed., "Sialic Acids," In *Cell Biology Monographs*, vol. 10:263–305 (1982).

Reuter, et al, "Suggestions on the Nomenclature of Sialic Acids", *Glycoconjugates* 5:133–135 (1988).

Roitt, et al., "Hypersensitivity–Type 1", *Immunology*, 19.1 (1985).

Sato, et al., "Bordetella Pertussis Infection in Mice: Correlation of Specific Antibodies Against Two Antigens, Pertussis Toxin, and Filamentous Hemagglutinin with Mouse protectivity in an Intracerebral for Aerosol Channel System", *Infect. Immun.*, 46:415–421 (1986).

Sauter, et al., *Biochem.*, 28:8388–8396 (1984).

Schwartz, et al., "Interaction Between Antigen–Presetting Cells and Primed T Lymphocytes: An Assessment of Ir Gene Expressions in the Antigen–Presenting Cell", *Immun. Rev.*, 40:153–180 (1978).

Seabrook, et al., "Recognition of Pertussis Toxin by Antibodies to Synthetic Peptides", *Molecular Immun.*, 27(8):777–785 (1990).

Sharon, "Lectin–Like Bacterial Adherence to Animal Cells", In *Attachment of Microorganisms to the Gut Mucosa*, (Boeheker, E.D., Ed.), pp. 129–147 (1984).

Siemann, In *Rodent Tumor Models in Exphel Cancer Therapy*, Ed. Kallman, pp. 13–15 (1987).

Sleytr, et al., "Structural and Chemical Characterization of S–layers of Selected Strains of *Bacillus Stearothermophilus* and *Desulfotomaculum Nigrificans*", *Arch. Microbiol.*, 146:19–24 (1986).

Smets, et al., "Tumor Cell Surface Carbohydrate," In *Membranes in Tumor Growth*, Galeotti, et al., Eds., pp. 77–81 (1982).

Smith, et al., "Cyclophosphamide and Dimethyl Dioctadecyl Ammonium Bromide Immunopotentiate the Delayed–Type Hypersensitivity Response to Inactivated Enveloped Viruses", *Immunology*, 58:245–250 (1986).

Smith, et al., "Induction of Delayed–Type Hypersensitivity to Measles Virus in Mice", *Cell. Immun.*, 89:20–29 (1984).

Springer, et al., "Sticky Sugars for Selectins", *Nature*, 349:196–197 (1991).

Tamura, et al., "A Role of the B–Oligomer Moiety of Islet–activating Protein, Pertussis Toxin, in Development of Biological Effects on Intact Cells", *J. Biol. Chem.*, 258:6756–6761 (1983).

Trinkaus, "The Molecular Structure of the Cell Surface", *Cells into Organs*, pp. 44–68 (1984).

Tuomanen, et al., "Receptor Analogs and Monoclonal Antibodies That Inhibit Adherence of Bordetella Pertussis To Human Ciliated Respiratory Epithelial Cells", *J. Exp. Med.*, 168:267–277 (1988).

Tuommenen, et al., "Bacterial Homologs of Selectins", *92nd General Meeting of the American Soc. of Microb.*, New Orleans, LA, Poster B–16 (1992).

Tyrrell, et al., "Lectinlike Properties of Pertussis Toxin", *Infect. Immun.*, 57:1854–1857 (1989).

Van't Wout, et al., *Infect. Immun.*, 60(8):3303–3308 (1992).

Walz, et al., "Recognition by ELAM–1 of the Sialyl–Le$^x$", *Science*, 250:1132 et seq. (1990).

Wang, et al., "The Immobilized Leukoagglutinin from the Seeds of Maackia Amurensis Binds with High Affinity to Complex–type Asn–linked Oligosaccharides Containing Terminal Sialic Acid–linked α–2,3 to Penultimate Galactose Residues", *J. Biol. Chem.*, 263:4576–4585 (1988).

Wassarman, "Fertilization", In *Cell Interactions and Development: Molecular Mechanisms* (Yamada, K.M., Ed.), pp. 1–27 (1983).

Wright, "2·2 A Resolution Structure Analysis of Two Refined N–acetylneuraminyl–lactose–Wheat Germ Agglutinin Isolectin Complexes", *J. Mol. Biol.*, 215:635–651 (1990).

Wright, "Structural Differences in the Two Mjor Wheat Germ Agglutinin Isolectins*", *J. Biol. Chem.*, 261(16):7191–7195 (1986).

* cited by examiner

| PEPTIDE | SEQ ID NO: | SEQUENCE |
|---|---|---|
| S2P1 | 3 (aa 9-23) | PQEQITQHGSPYGRC |
| ACS2P1 | 3 (aa 9-23) | PQEQITQHGSPYGRC-CO-NH$_2$ |
| S2P2 | 3 | STPGIVIPPQEQITQHGSPYGRC |
| SPYGRC | 3 (aa 18-23) | SPYGRC-CO-NH$_2$ |
| SPYGRC-b | 3 (aa 18-23) | BIOTIN-SPYGRC-CO-NH$_2$ |
| S2P3 | 4 | GAFDLKTTFCIMTTRNTGQPA |
| S2P6 | 5 | FVRSGQPVIGACTSPYDGKYWSMYSRLRKMLY |
| S3P1 | 6 (aa 9-23) | PKALFTQQGGAYGRC |
| S3P9a | 9 | RLLASTNSRLCAVFVRDG |
| S2(WGA)# | 10 | PQEQITQHGSQYGYC |
| WGA(62-73) | 11 | SQYGYCGFGAEY |

FIG. 1 aa amino acids

ANTI-FLAMMATORY CARBOHYDRATE BINDING-PEPTIDES

CROSS-REFERENCE TO RELATED APPLICATIONS

This application is a continuation, of application Ser. No. 08/390,509, filed Feb. 17, 1995, now U.S. Pat. No. 5,833,990 which is a continuation of U.S. Ser. No. 07/995,503, filed Dec. 21, 1992, now U.S. Pat. No. 5,453,272, which is a continuation-in-part of U.S. Ser. No. 07/956,043, filed Oct. 2, 1992, now abandoned.

BACKGROUND OF THE INVENTION

1. Field of the Invention

This invention is directed to methods for inhibiting immune responses or cellular interactions in mammals by the administration thereto of one or more lectin derived carbohydrate binding peptides. In particular, this invention is directed to methods for the suppression of inflammatory responses, induction of tolerance to antigens, modulation of the induction of immune responses to antigens, and the inhibition of cell adhesion in mammals by the administration of one or more carbohydrate binding peptides. The lectin derived carbohydrate binding peptides employed herein are preferably fragments of the S2 or S3 subunits of the pertussis toxin expressed by *Bordetella pertussis* or functionally equivalent variants thereof.

2. References

The following references are cited in this application as superscript numbers at the relevant portion of the application:

1. Brandley, et al., *J. Leukocyte Biol.,* 40:97–111 (1986).
2. Jacobson, *Developmental Neurobiology,* New York, Plenum Press p. 5–25, (1978).
3. Trinkaus, *Cells into Organs,* Englewood Cliffs, N.J., Prentice Hall, p. 44–68, (1984).
4. Frazier, et al., *Annu. Rev. Biochem.,* 48:491 (1979).
5. Glaser, *Mediator of Developmental Processes* (Substency, S. And Wessels, N. K., Eds.) New York, Academic Press, p. 79 (1980).
6. Paulson, *In "The Receptors",* Vol. II (Comm., P. M., Ed.), New York Academic Press, p. 131 (1985).
7. Sharon, *Lectin-Like Bacterial Adherence to Animal Cells.* In "Attachment of Microorganisms to the Gut Mucosa" (Boeheker, E. D., Ed.), Boca Raton, Fla. CRC Press, p. 129 (1984).
8. Wassarman, *Fertilization.* In "Cell Interactions and Development: Molecular Mechanisms" (Yamada, K. M., Ed.), New York, John Wiley and Sons, p. 1 (1983).
9. Schwartz, et al., *Immunol. Rev.,* 40:153 et seq. (1978).
10. Coutinho, et al., *Immunol. Rev.,* 78:211 et seq. (1984).
11. Hoffmann, et al., Eds., *Membranes in Growth and Development,* New York, Alan R. Liss, p. 429–442, (1982).
12. Galeotti, et al., Eds., *Membranes in Tumor Growth,* Amsterdam, Elsevier, p. 77–81, (1982).
13. Nicolson, et al., *Invas. Metas.,* 5:144 et seq. (1985).
14. Aplin, et al., *Biochim. Biophys. Acta* 694:375 et seq. (1982).
15. Barondes, *Developmentally Regulated Lectins.* In "Cell Interactions and Development: Molecular Mechanisms" (Yamada, D. M., Ed.) New York, John Wiley and Sons, p. 185 (1983).
16. Monisigny, M., Ed., *Biol. Cell,* 51 (Special Issue), 113 et seq., 1984.
17. Springer, et al., *Nature,* 349:196–197 (1991).
18. Lowe, et al., *Cell,* 63:475–485 (1990).
19. Phillips, et al., *Science,* Vol. 250:1130–1132 (1990).
20. Walz, et al., *Science,* 250:1132 et seq. (1990).
21. Larsen, et al., Cell, 63:467–474 (1990).
22. Bevilacqua, et al., *Endothelial-Leukocyte Adhesion Molecule*-1 (*ELAM*-1): *A Vascular SELECTIN That Regulates Inflammation.* In "Cellular and Molecular Mechanisms of Inflammation" Vol. 2, Academic Press, p. 1–13 (1991).
23. McEver, *Leukocyte Interactions Mediated by GMP*-140. In "Cellular and Molecular Mechanisms of Inflammation", Vol. 2, Academic Press, p. 15–29 (1991).
24. Larsen, et al., *J. Biol. Chem.,* 267:11104–11110 (1992).
25. Heerze, et al., *Biochem and Biophys. Res. Comm.* 172:1224–1229 (1990).
26. Paulson, et al., International Patent Application Publication No. WO91/19502, (1991).
27. Ippolito, et al., U.S. patent application Ser. No. 07/714, 161, filed Jun. 10, 1991.
28. Ippolito, et al., U.S. patent application Ser. No. 07/889, 017, filed May 26, 1992.
29. McEver, International Patent Application Publication No. WO92/01718, filed Jul. 17, 1991.
30. Heerze, et al., *Biochem and Biophys. Res. Comm.,* 179:1464–1469 (1991).
31. Pearce-Pratt, et al., *J. Imm. Methods,* 140:159–165 (1991).
32. Smith, et al., *Cell. Imm.,* 89:20–29 (1984).
33. Munoz, *Action of Pertussigen* (*Pertussis Toxin*) *on the Host Immune System.* In "Pathogenesis and Immunity in Pertussis", John Wiley & Sons Ltd., p. 173–192 (1988).
34. Reuter, et al, *Glycoconjugates* 5:133–135 (1988).
35. Gaeta, et al., U.S. patent application Ser. No. 07/538, 853, filed June 15, 1990.
36. Paulson, et al., U.S. patent application Ser. No. 07/619, 319, filed Nov. 28, 1990.
37. Paulson, et al., U.S. patent application Ser. No. 07/632, 390, filed Dec. 21, 1990.
38. Brandley, et al., PCT International Patent Application No. PCT/US91/05416, published Feb. 20, 1992.
39. Lowe, PCT International Patent Application No. PCT/US91/07678, published May 14, 1992.
40. Furie, et al., PCT International Patent Application No. PCT/US92/01915, published Oct. 1, 1992.
41. Seed, et al., PCT International Patent Application No. PCT/US91/08685, published Jun. 11, 1992.
42. Karlsson, *Annu. Rev. Biochem.,* 58:309–350 (1989).
43. Brennan, et al., *J. Biol. Chem.,* 263:4895–4899 (1988).
44. Armstrong, et al., *J. Biol. Chem.,* 263:8677–8684 (1988).
45. Smith, et al., U.S. patent application Ser. No. 07/956, 043, filed Oct. 2, 1992.
46. Shibuya, et al., *J. Biol. Chem.,* 261:7755–7761 (1987).
47. Wang, et al., *J. Biol. Chem.,* 263:4576–4585 (1988).
48. Gimbrone, et al., International Patent Application Publication No. WO 91/08231.
49. Ratcliffe, et al., U.S. Pat. No. 5,079,353, issued Jan. 7, 1992.
50. Hakomori, *Adv. Cancer Res.,* 52:257–331 (1989).
51. Sialic Acids in "*Cell Biology Monographs*", Schauer, Editor, Vol. 10 (1982).
52. Tyrrell, et al., *Infect. Immun.,* 57:1854–1857 (1989).
53. Bhavanandan, et al., *J. Biol. Chem.,* 254:4000–4008 (1979).
54. Nogimori, et al., *Biochemistry,* 25:1355–1363 (1986).
55. Sato, et al., *Infect. Immun.,* 46:415–421 (1986).
56. Tamura, et al., *J. Biol. Chem.,* 256:6756–6761 (1983).
57. Tuomanen, et al., *J. Exp. Med.,* 168:267–277 (1988).

58. Tuommenen, et al., *92nd General Meeting of the American Society of Microbiology*, New Orleans, La., Poster B-16.
59. Morgan, et al., *Ann. Repts. Med. Chem.*, 24:243–252 (1989).
60. Chou, et al., *Annu. Rev. Biochem.*, 47:251–276 (1978).
61. Hopp, et al., *Proc. Natl. Acad. Sci. U.S.A.*, 78:3824–3828 (1981).
62. Wright, J. Mol. Biol., 215:635–651 (1990).
63. Armstrong, et al., *Infect. Immun.*, 55:1294–1299 (1987).
64. Smith, et al., *Immunology*, 58:245 et seq. (1986).
65. Sleyter, et al., *Arch. Microbiol.*, 146:19 et seq. (1986).

The disclosure of all publications, patents and patent applications cited in this application are herein incorporated by reference in their entirety to the same extent as if each individual publication or patent application was specifically and individually indicated to be incorporated by reference in its entirety.

3. State of the Art

Important processes involving mammalian cells, such as growth, locomotion, morphological development, and differentiation are partially controlled by extracellular signals acting upon the cells' surfaces[1-3]. While some external stimuli reach the cell via extracellular fluids, other signals are received from neighboring or approaching cell surfaces and exert their effects through direct cell-cell contact[4,5].

Evidence suggests that specific cell-surface receptors can "sense" a molecular signal of an apposing cell via specific binding, and biochemical mechanisms exist to translate that binding into a cellular response. For example, complex cell-surface interactions are believed to help direct processes such as binding of pathogens to target tissues[6,7], sperm-egg binding[8], interactions among cells in the immune system[9,10], and recognition of cells during embryonic development[11]. In addition, defects in cell-cell recognition are thought to underlie the uncontrolled cell growth and motility which characterize neoplastic transformation and metastasis[12,13].

Other evidence suggests that cell-recognition processes are mediated by carbohydrate chains or glycan portions of glycoconjugatest[4,14-16]. For example, the binding of the surface glycoconjugates of one cell to the complementary carbohydrate-binding proteins (lectins) on another cell can result in the initiation of a specific interaction.

One important group of carbohydrate-binding proteins are selectin (LEC-CAM) proteins (Lectin+EGF+ complementary Regulatory Domain-Cell Adhesion Molecules). These or functionally similar proteins or lectins are believed to play a critical role in immune responses (including inflammatory responses) through mediation of cell-cell contact and through extra-vasation of leucocytes[17-22]. Specific carbohydrate ligands have been identified as part of the putative receptor structures for selectin proteins and other lectins[17-25]. The structures identified include oligosaccharide glycosides containing terminally linked α-sialic acid(2→6)βGal- and α-sialic acid(2→3)βGal-groups. The use of oligosaccharides and derivatives thereof having such terminally linked groups for controlling inflammation, immunosuppression, etc. by interacting with selectin proteins and/or other lectins has been disclosed[26-29,35-41].

Likewise, peptides derived from the selectin GMP-140 which inhibit binding of GMP-140 and other selectins to leukocytes, presumably by interfering with the binding of the GMP-selectin protein with the carbohydrate receptor on the leukocyte, have also been disclosed as being useful in suppressing an immune response[29]. Similarly, other peptides are also known to be potent modulators of neutrophil functions[48].

Pertussis toxin (PT)[42], a virulence factor produced by the organism *Bordetella pertussis*—the etiological agent of whooping cough, is known to bind to glycoprotein receptors which terminate in sialyllactosamine sugar sequences[43,44] and we have previously shown that this protein is useful in suppressing mammalian immune responses and cellular adhesion[45]. PT's binding specificity has been shown to be similar to that of the plant lectins from *Sambucus nigra* (SNA) and *Maackia amurensis* (MAL)[25], which bind with high affinity to sialic acid-containing glycoconjugates[46,47] and which have also been shown as possessing immuno-modulating properties[45].

However, the use of proteins or large molecular weight polypeptides in inhibiting immune responses or cellular interactions in mammals suffers from several drawbacks, including the fact that they are difficult to produce in large quantities in pure form; that they tend to produce adverse affects when repeatedly administered to a mammal; that they can contain infectious agents or toxic substances which are contra-indications to mammalian administration; and, that it is difficult to modify the pharmokinetic properties of such proteins to improve their efficacy.

In view of the above, the use of peptides having lectin-like binding properties for terminal αNeu5Ac(2→3)βGal- and αNeu5Ac(2→6)βGal- groups would be particularly beneficial for use in inhibiting immune responses and cellular interactions in mammals as compared to the administration of proteins such the pertussis toxin and the lectins derived from SNA and MAL because such peptides would mitigate the problems associated with the administration of proteins and large molecular weight polypeptides to mammals.

SUMMARY OF THE INVENTION

This invention is directed, in part, to the discovery that the binding domains for the α-sialic acid(2→3)βGal- and/or the α-sialic acid(2→6)βGal-terminally linked structures are found in certain peptide fragments of lectins (e.g., proteins and polypeptides) such as pertussis toxin and that it is not necessary to employ the entire lectin to effect binding to these carbohydrates (oligosaccharides).

This invention is further directed, in part, to the discovery that, when these lectin derived carbohydrate binding peptides are administered to a mammal (e.g., human) in effective amounts, they inhibit specific immune responses and cellular interactions. In particular, this invention is directed to the discovery that such lectin derived carbohydrate binding peptides may be administered to a mammal in order to inhibit inflammatory responses, modulate the induction of an immune response to an antigen, induce long term tolerance to an antigen, and suppress cell adhesion.

This invention is particularly directed to the discovery that lectin derived carbohydrate binding peptides capable of binding terminally linked α-sialic acid(2→3)βGal- and/or α-sialic acid(2→6)βGal- (e.g., αNeu5Ac(2→3)βGal-) groups present in molecules (e.g., oligosaccharides, glycoproteins, glycolipids, etc.) which can be found on cell surfaces (e.g., leukocytes) may be administered to a mammal as a means for inhibiting cell adhesion or cell-mediated immune responses. Cell-mediated immune responses inhibited by the peptides disclosed herein include inflammatory responses, modulation of the induction of the immune response to an antigen and the induction of long term tolerance to an antigen.

Preferably, the lectin derived carbohydrate binding peptides employed herein are fragments of the S2 or S3 subunits of the pertussis toxin expressed by *Bordetella pertussis* or functionally equivalent variants thereof. These preferred peptides have the amino acid sequences set forth in peptides of FIG. 1 below.

Accordingly, in one of its method aspects, this invention is directed to a method of suppressing a inflammatory response in a mammal by the administration of an effective amount of at least one lectin derived carbohydrate binding peptide or derivative thereof capable of binding a terminally linked α-sialic acid(2→6)βGal- and/or α-sialic acid(2→3)βGal- groups on structures or molecules comprising such groups.

In another of its method aspects, this invention is directed to a method for modulating the induction of an immune response to an antigen in a mammal by administering the antigen in combination with an effective amount of at least one lectin derived carbohydrate binding peptide or derivative thereof capable of binding terminally linked α-sialic acid(2→6)βGal- and/or α-sialic acid(2→3)βGal- groups on structures or molecules comprising such groups.

In another of its method aspects, this invention is directed to a method for inducing in a sensitized mammal long term tolerance to an antigen by exposing (challenging) the mammal with the antigen followed by the administration of an effective amount of at least one lectin derived carbohydrate binding peptide or derivative thereof capable of binding terminally linked α-sialic acid(2→6)βGal- and/or α-sialic acid(2→3)βGal- groups on structures or molecules comprising such groups.

In still another one of its method aspects, this invention is directed to a method for inhibiting cell adhesion events involved in metastasis of tumor cells or in inflammation by the administration of an effective amount of at least one lectin derived carbohydrate binding peptide or derivative thereof capable of binding terminally linked α-sialic acid (2→6)βGal- and/or α-sialic acid(2→3)βGal- groups on structures or molecules comprising such groups.

In yet another one of its method aspects, this invention is directed to a method for treating lung inflammation and/or lung injury in a mammal by the administration of an effective amount of one or more lectin derived carbohydrate binding peptides or derivative thereof capable of binding terminally linked α-sialic acid(2→6)βGal- and/or α-sialic acid(2→3)βGal-groups on structures or molecules comprising such groups.

In its composition aspects, this invention is directed to pharmaceutical compositions comprising the subject lectin derived carbohydrate binding peptides including pharmaceutically acceptable salts of such lectin derived carbohydrate binding peptides.

BRIEF DESCRIPTION OF THE DRAWINGS

FIG. 1 illustrates the amino acid sequence of preferred lectin derived carbohydrate binding peptides.

In FIGS. 2 and 3, peptide 2275 is ACS2P1 (amino acids 9–23 of SEQ ID NO:3) and peptide 2283 is SPYGRC (amino acids 18–23 of SEQ ID NO:3) both of which are illustrated in FIG. 1.

Figure 2:
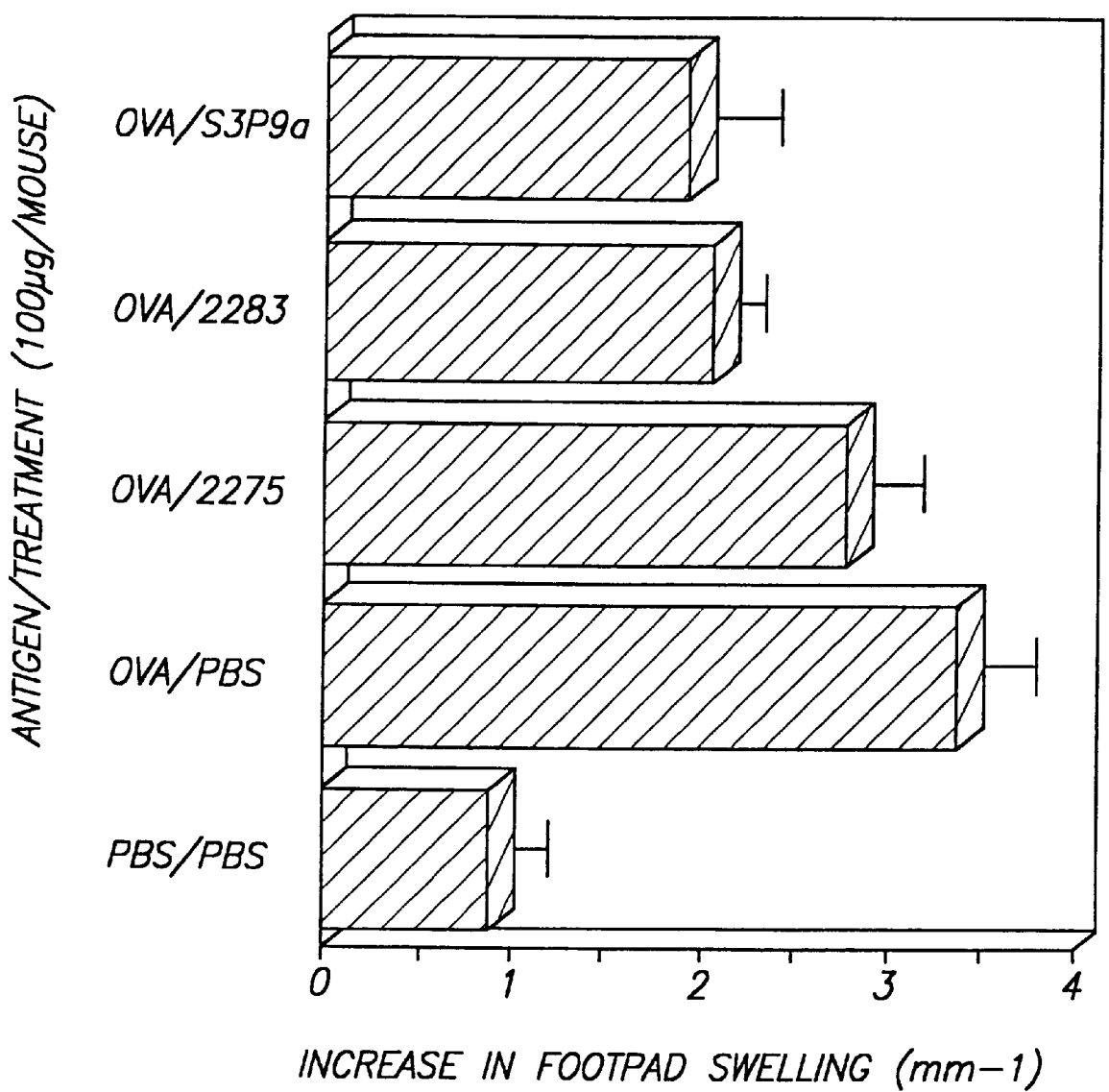
FIG. 2 illustrates the increase in footpad swelling of immunized Balb/c mice arising from a DTH inflammatory response measured 24 hours after challenge with 20 µg of OVA antigen wherein some of the mice have been treated at 5 hours after challenge with 100 µg of a lectin derived carbohydrate binding peptide.

The amino acid residues depicted in FIG. 1 and used throughout this application are designated by the conventional single letter code set forth below:

| | |
|---|---|
| A | alanine |
| C | cystine |
| D | aspartic acid |
| E | glutamic acid |
| F | phenyl alanine |
| G | glycine |
| H | histidine |
| I | isoleucine |
| K | lysine |
| L | leucine |
| M | methionine |
| N | asparagine |
| P | proline |
| Q | glutamine |
| R | arginine |
| S | serine |
| T | threonine |
| V | valine |
| w | tryptophane |
| Y | tyrosine |

Additionally, as conventionally indicated, the amino acid residue forming the $H_2N$— terminus of the peptide is set forth on the left side of the peptide chain and the —COOH terminus of the peptide is set forth on the right side of the peptide chain.

DETAILED DESCRIPTION OF THE PREFERRED EMBODIMENTS

This invention is directed, in part, to the discovery that certain lectin derived carbohydrate binding peptides when administered to a mammal are effective in suppressing inflammatory responses, inducing tolerance to an antigen, modulating the induction of immune responses to antigens, and inhibiting cell adhesion events, e.g., cell adhesion events involved in metastasis of tumor cells.

1. Definitions

As used herein, the following terms have the meanings set forth below:

The term "inflammatory response" or "inflammatory disorder" will refer to immune reactions involving specific and non-specific defense systems. A specific defense system reaction is a specific immune system reaction to an antigen. Examples of specific defense system reactions include antibody responses to antigens, such as viruses, allergens, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of polymorphonuclear (PMN) leukocytes at sites of bacterial infection (e.g., pulmonary infiltrates in bacterial pneumonias and pus formation in abscesses).

Other "inflammatory responses" or "inflammatory disorders" within the scope of this invention include, e.g., autoimmune disorders such as rheumatoid arthritis, lupus, multiple sclerosis, post-ischemic leukocyte mediated tissue damage (reperfusion injury), frost-bite injury or shock, acute leukocyte-mediated lung injury (ARDS), asthma, traumatic shock, septic shock, nephritis, and acute and chronic inflammation, including atopic dermatitis, psoriasis, and inflammatory bowel disease. Various platelet-mediated pathologies such as atherosclerosis and clotting are also included within the definition of "inflammatory responses" or "inflammatory disorders". In addition, "inflammatory responses" or "inflammatory disorders" may include the adhesion of circulating cancer cells, with specific examples including carcinoma of the colon and melanoma.

Without being limited to any theory, we believe that primary events in the initiation of such inflammatory responses and inflammatory disorders are the binding of leukocytes to selectins (e.g., ELAM-1, PADGEM, etc.) through carbohydrate receptors comprising α-sialic acid (2→3)βGal- and/or α-sialic acid(2→6)βGal-groups[35-40] found on the surface of the leukocytes. Likewise, it has been shown that mammalian and, in particular, human cancer cells contain α-sialic acid(2→3)βGal- and/or α-sialic acid (2→6)βGal- groups on the surface thereof[49,50] and it is believed that binding of such circulating cancer cells to selectins is an integral part of the metastatic process[36,37]. Accordingly, by interfering with the binding of such carbohydrate receptors to these selecting, suppression of the inflammatory immune responses as well as inhibition of metastatic processes is achieved.

The term "antigen" refers to any protein, peptide, carbohydrate, nucleic acid or other non-endogenous substance which when exposed to a mammal induces an immune response in that mammal.

Disease conditions believed to be caused by antigen exposure include, by way of example, psoriasis, asthma, dermatitis, rheumatoid arthritis, delayed type hypersensitivity, inflammatory bowel disease, multiple sclerosis, viral pneumonia, bacterial pneumonia, and the like.

The term "non-sensitized mammal" refers to those mammals which have yet to be educated to a particular antigen.

The term "sensitized mammal" refers to those mammals which have been previously exposed to a particular antigen and, accordingly, their immune systems have become educated to that antigen. Typically, initial exposure of an antigen to a mammal primes or educates the mammal's immune response to later exposure to that antigen with minimal inflammation during such initial exposure.

The term "secondary immune response" refers to the effector phase of a mammal's immune response to an antigen to which it has been previously been sensitized. A mammal's secondary immune response is typically accompanied by inflammation at the point of antigen exposure.

"Acute respiratory distress syndrome" or "ARDS" refers to an inflammatory condition comprising leukocyte mediated lung injury. Without being limited to any theory, it is believed that such lung injury is exacerbated by infiltration and subsequent disruption of neutrophils into the lungs. Specifically, the disruption of the neutrophils in the lungs releases superoxides which results in severe vascular endothelial damage. Accordingly, while this lung damage is not antigen based, the infiltration of neutrophils into the lungs requires an adhesion event.

"Reperfusion injury" refers to an inflammatory condition comprising leukocyte mediated tissue damage. Reperfusion injury commonly occurs after myocardial infarction wherein, in response to the inflammation caused by the myocardial infarction, the endothelium cells are activated and produce selectins (e.g., ELAM-1). In turn, neutrophils are then capable of binding the selectins expressed on the vascular endothelium and cause further damage.

The term "pertussis toxin" or "PT" in this application refers to the virulence factors produced by Bordetella pertussis, the etiological agent of whooping cough. The β-oligomer of PT binds to both α-sialic acid(2→6)βGal- and α-sialic acid(2→3)βGal- structures. PT also has similar binding characteristics to those of wheat germ agglutinin (WGA), which can recognize terminal N-acetylglucosamine (GlcNAc) saccharide sequences in addition to sialic acid[44, 52,53].

PT is a classical A-B type of toxin comprised of an A subunit (designated Si) that contains an ADP-ribosyltransferase enzyme activity, which is responsible for most of the biological effects of PT[54]. The lectin-like activity is found in the complex β oligomer of PT, which consists of four heterogeneous subunits that are arranged in a pair of dimers (S2–S4 (Dimer 1) and S3–S4 (Dimer 2)) joined by a smaller S5 subunit. The functioning of the β oligomer is in binding to host cell sialylated oligosaccharide receptors as well as providing a delivery system for the A subunit through the cytoplasmic membrane[54,55,56]. The β oligomer itself can induce a mitogenic response in lymphocytes and has the ability to agglutinate erythrocytes. PT may also contribute to the attachment of B. pertussis to epithelial cells lining the upper respiratory tract of humans; the only known host of B. pertussis[57]. In addition, the β oligomer also appears to share functional homology with the selectin family of mammalian lectins that regulate leukocyte trafficking.[58]

The term "cell-mediated immune response" refers to those mammalian immune responses which are mediated by cell-cell interactions. Included within this term are cell-mediated inflammatory responses to an antigen including, by way of example, such responses as delayed-type hypersensitivity (DTH) responses, virus-induced pneumonia, allergic responses, and the like as well as cell-mediated inflammatory responses arising from injuries such myocardial infarction, shock and sequelae (e.g., multiple organ failure), acute respiratory distress syndrome, (ARDS), and the like. Generally, the cell-mediated immune response is a leukocyte-mediated response.

The term "humoral immune response" refers to mammalian immune responses which involve antigen-antibody interactions.

The term "DTH inflammation response" or delayed type hypersensitivity response is a T cell mediated reaction which results in a mononuclear cell-rich inflammation and swelling which occurs after antigenic challenge.

The term "tolerance" or "immunological tolerance" refers to a reduced immunogenic response elicited in a sensitized mammal to a particular antigen upon a second or subsequent antigenic challenge in comparison to the primary immune response elicited by said antigen under equivalent conditions (e.g., dosage). In the present invention such "tolerance" will be obtained by administration of an antigen to the sensitized mammal followed by administration of one or more lectin derived carbohydrate binding peptides which bind to α-sialic acid(2→6)βGal- and/or α-sialic acid(2→3)βGal- structures.

The term "period for maximal inflammation" refers to the period of time typically required to achieve maximal inflammation in a mammal due to a cell-mediated immune response including both cell-mediated inflammatory responses in a sensitized mammal due to antigen exposure (challenge) and cell-mediated inflammatory responses in a mammal due to injury (e.g., myocardial infarction). This period of time depends on several factors such as the specific antigen/injury afflicting the mammal; the particular mammalian species exposed to the antigen/injury, etc. Accordingly, the period of time required to effect maximal inflammation will vary for, by way of example, rheumatoid arthritis as opposed to myocardial infarction.

Moreover, while the specific time required to effect maximal inflammation will vary somewhat in a given mammalian species, the time typically required to effect maximal inflammation for different afflictions due to either antigen exposure or injury in human and other mammals is known in the art or are readily ascertainable by the skilled artisan. For example, in the case of a DTH response in mice, maximal inflammation is typically 24 hours after antigen exposure.

The term "sialic acid" refers to all naturally occurring structures of sialic acid and analogues of sialic acid as well as derivatives thereof. Naturally occurring structures of sialic acid include, by way of example, 5-acetamido-3,5-dideoxy-D-glycero-D-galacto-nonulopyranosylonic acid ("Neu5Ac"), N-glycoyl neuraminic acid (Neu5Gc) and 9-O-acetyl neuraminic acid (Neu5,9Ac$_2$). A complete list of naturally occurring sialic acids known to date are provided by Schauer[51].

Derivatives of sialic acid refers to derivatives of naturally occurring structures of sialic acid including those wherein the sialic acid unit has been chemically modified so as to introduce and/or remove one or more functionalities from such structures. For example, such modification can result in the removal of an —OH functionality, the introduction of an amine functionality, the introduction of a halide functionality, and the like.

Certain derivatives of sialic acid are known in the art and include chemically modified sialic acid derivatives such as 9-azido-Neu5Ac, 9-amino-Neu5Ac, 9-deoxy-Neu5Ac, 9-fluoro-Neu5Ac, 9-bromo-Neu5Ac, 8-deoxy-Neu5Ac, 8-epi-Neu5Ac, 7-deoxy-Neu5Ac, 7-epi-Neu5Ac, 7-8-bis-epi-Neu5Ac, 4-O-methyl-Neu5Ac, 4-N-acetyl-Neu5Ac, 4,7-di-deoxy-Neu5Ac, 4-uno-Neu5Ac, 3-hydroxy-Neu5Ac, 3-fluoro-Neu5Ac acid as well as 6-thio analogues of Neu5Ac are known in the art. Methods for preparing such sialic acid derivatives are taught in commonly assigned, U.S. Ser. No. 07/889,017, filed on May 26, 1992, which application is incorporated by reference in its entirety.

The nomenclature describing derivatives of sialic acid derivatives herein is as set forth by Reuter et al[34].

The term "α-sialic acid(2–6)βGal-structures or groups" refer to molecules comprising the terminally linked α-sialic acid(2→6)galactose-sequence or derivatives thereof. Molecules containing such terminal structures have been identified as comprising part of the putative receptor structure for the ELAM-1 and PADGEM selectins[38,40].

The term "α-sialic acid(2→3)βGal-structures or groups" refer to molecules comprising the terminally linked α-sialic acid(2→3)galactose-sequence or derivatives thereof. Molecules comprising such terminal structures have similarly been identified as comprising part of the putative receptor structures for the ELAM-1 selectins[35-39].

The term "lectin derived carbohydrate binding peptide" refers to any peptide or derivative thereof (including pharmaceutically acceptable salts) derived from a lectin and which is capable of binding to α-sialic acid(2→6)βGal- and/or α-sialic acid(2→3)βGal-carbohydrate structures which are preferably comprised on the surface of mammalian cells. Generally, in the present application, "lectin derived carbohydrate binding peptide" will refer to such peptides which, in monomeric form, have no more than about 35 amino acids in the lectin-like domain (i.e., the part of the peptide responsible for binding to such carbohydrate structures). Suitable derivatives of lectin derived carbohydrate binding peptides include those peptides which have the NH$_2$ and/or the COOH terminal functionalities blocked by conventionally blocking groups as well as derivatives which include modifications, deletions or derivatizations of one or more of the amino acids that yield a peptide which is capable of binding to α-sialic acid(2→6)βGal- and/or α-sialic acid (2→3)βGal-structures.

More preferably, the lectin derived carbohydrate binding peptides refer to the peptides set forth in FIG. 1.

Still more preferably, the lectin derived carbohydrate binding peptides are peptides which have a high degree of homology with a lectin-like binding domain for the α-sialic acid(2→6)βGal- and/or α-sialic acid(2→3)βGal-carbohydrate structures found in the pertussis toxin. These peptides are represented by formula I (SEQ ID NO:1):

$$SPX_1GX_2C \qquad\qquad I$$

where $X_1$ is selected from the group of amino acids Y, F, W, and H or peptide mimetics thereof, and $X_2$ is selected from the group consisting of amino acids Y, F, R, W, and H or peptide mimetics thereof;

or by formula II (SEQ ID NO:2):

$$SPX_1GX_2CX_3X_4 \qquad\qquad II$$

where $X_1$ is selected from the group of amino acids Y, F, W, and H or peptide mimetics thereof, $X_2$ is selected from the group consisting of amino acids Y, F, R, W, and H or peptide mimetics thereof;

$X_3$ is an amino acid sequence of 4–6 amino acids; and $X_4$ is selected from the group consisting of amino acids Y, F, W, and H or peptide mimetics thereof.

Most preferably, the lectin derived carbohydrate binding peptide refers to the hexapeptide SPYGRC (amino acids 18–23 of SEQ ID NO:3).

In addition to their use as modulating agents for mammalian immune and cellular adhesion processes, the lectin derived carbohydrate binding peptides described herein can further be used in assay methods for determining the presence of α-sialic acid(2→3)βGal- and/or α-sialic acid(2→6) βGal-structures on molecules and/or cell surfaces such as in suspected cancer cells; for determining the relative binding affinity of peptides and/or proteins to α-sialic acid(2→3) βGal- and/or α-sialic acid(2→6)βGal-structures; and the like. When so employed, the lectin derived carbohydrate binding peptides typically will be derivatized to include a label or a label binding moiety.

Suitable labels are well known in the art and include, by way of example, enzymes (e.g., horseradish peroxidase), radioisotopes (e.g., $^{125}I$), fluorescent moieties, chemiluminscent moieties, and the like. The particular label employed is not critical and methods for attaching labels to peptides are well known in the art.

Suitable label binding moieties are also well known in the art and include, by way of example, biotin, avidin, streptavidin antibodies, etc. A preferred label binding moiety is biotin which permits binding of up to 4 peptide/biotin adducts to avidin. The avidin can be appropriately labeled so that resulting peptide/biotin/avidin complex can be detected.

The term "lectins" refer to carbohydrate binding proteins of non-immune origin often obtained from plants or bacterial or viral microorganisms which comprise carbohydrate binding sites. These binding proteins typically comprise the ability to agglutinate cells and to precipitate complex carbohydrates. Lectins are classified based upon their carbohydrate binding specificity and are well known in the art.

The term "lectin-like domain" refers to those fragment(s) of a lectin responsible for binding the carbohydrate.

The term "pharmaceutically acceptable salts" includes the pharmaceutically acceptable addition salts of lectin derived carbohydrate binding peptides capable of binding to terminally linked α-sialic acid(2→6)βGal- and/or α-sialic acid (2→3)βGal-. Such pharmaceutically acceptable addition salts may be derived from a variety of organic and inorganic counter salts well known in the art and include, by way of example only, sodium, potassium, calcium, magnesium, ammonium, tetralkyl-ammonium, and the like.

2. Utility

Without being limited to any theory, it is believed that the subject lectin derived carbohydrate binding peptides affect the immune response in a number of ways. Lectin derived carbohydrate binding peptides can inhibit a mammal from becoming "educated" about a specific antigen when the lectin derived carbohydrate binding peptide is administered simultaneously with the first exposure of the immune system to the antigen.

The lectin derived carbohydrate binding peptides can reduce cell-mediated immune responses to injury such as inflammatory responses arising from myocardial infarction, ARDS, frost bite, etc. The lectin derived carbohydrate binding peptides can also inhibit the effector phase of a cell-mediated immune response (e.g., the inflammatory component of a DTH response) when administered to a sensitized mammal after exposure of the sensitized mammal's immune system to the antigen. In either case, in order to effect reduction in the cell-mediated immune response, it is necessary to administer the lectin derived carbohydrate binding peptides after initiation of the mammal's immune response and at or prior to one-half the period required for maximal inflammation induced by the injury or the antigen exposure.

Additionally, the subject lectin derived carbohydrate binding peptides can induce tolerance to antigens in sensitized mammals when administered at the time of second or later exposures of the immune system to the antigen when administration is conducted after initiation of the mammal's secondary immune response to the antigen and at or prior to one-half the period required for maximal inflammation induced by the antigen exposure.

Further, the administration of lectin derived carbohydrate binding peptides that bind α-sialic acid(2→6)βGal- and/or α-sialic acid(2→3)βGal-structures inhibit the binding of LEC-CAM proteins and other selectins to their putative receptors therefor which include both the α-sialic acid (2→6)βGal-[38,40] and the α-sialic acid(2→3)βGal-[35-39] structures.

Accordingly, the subject invention provides both pharmaceutical compositions containing lectin derived carbohydrate binding peptides capable of binding terminally linked α-sialic acid(2→6)βGal- and the α-sialic acid(2→3)βGal-structures which are useful in inhibiting specific immune responses or cellular interactions in mammals as well as methods which include the administration of such lectin derived carbohydrate binding peptides to a mammal for inhibiting a cell-mediated immune response.

As noted above, lectin derived carbohydrate binding peptides useful for modulating a cell-mediated immune response in a mammal include any lectin derived peptide or derivative thereof capable of binding terminally linked α-sialic acid(2→6)βGal- and the α-sialic acid(2→3)βGal-structures. Suitable lectin derived carbohydrate binding peptides preferably are peptides which, in monomeric form, have no more than about 35 amino acids in the lectin-like domain (i.e., the part of the peptide responsible for binding to such carbohydrate structures).

More preferably, the lectin derived carbohydrate binding peptides refer to the peptides set forth in FIG. 1.

Still more preferably, the lectin derived carbohydrate binding peptides are peptides which have a high degree of homology with a lectin-like binding domain for terminally linked α-sialic acid(2→6)βGal- and/or α-sialic acid(2→3) βGal-carbohydrate structures found in the pertussis toxin. These peptides are represented by formula I (SEQ ID NO:1):

$$SPX_1GX_2C \qquad \qquad I$$

where $X_1$ is selected from the group of amino acids Y, F, W, and H or peptide mimetics thereof, and $X_2$ is selected from the group consisting of amino acids Y, F, R, W, and H or peptide mimetics thereof;

or by formula II (SEQ ID NO:2):

$$SPX_1GX_2CX_3X_4 \qquad \qquad II$$

where $X_1$ is selected from the group of amino acids Y, F, W, and H or peptide mimetics thereof, $X_2$ is selected from the group consisting of amino acids Y, F, R, W, and H or peptide mimetics thereof;

$X_3$ is an amino acid sequence of 4–6 amino acids; and $X_4$ is selected from the group consisting of amino acids Y, F, W, and H or peptide mimetics thereof.

The preparation of such peptides is well known in the art and includes, by way of example, standardized commercially available peptide synthesizers such as Model ABI 403A available from Applied Biosystems, Inc., Foster City, Calif. The methods for preparing such peptides does not form a part of this invention.

Peptide mimetics refer to groups which mimic an amino acid in the peptide chain. Such mimetics and their synthesis are well known in the art[59].

The lectin derived carbohydrate binding peptides can be used either in monomeric or polymeric form. Examples of suitable polymers include the attachment of biotin to the lectin derived carbohydrate binding peptide followed by complexing with avidin which results in up to a tetravalent complex. Likewise, multivalent derivatives of lectin derived carbohydrate binding peptides can be synthesized by attaching such peptides to polymers such as polylysine or an inert protein such as human serum albumin. The multivalent derivatives so formed can contain one or a mixture of different lectin derived carbohydrate binding peptides so as to enhance efficacy.

In the case of protein peptide conjugates, they will be chemically cross-linked with the carrier protein by known cross-linking agents using art recognized methodology.

In yet another embodiment, multivalent lectin derived carbohydrate binding peptides can be generated as a copolymer wherein the peptides are linked together through a spacer arm to provide for a repeating subunit represented by the groups:

[carbohydrate binding peptide-spacer arm]$_n$

[carbohydrate binding peptide]$_n$-spacer arm

In these subunits, the lectin derived carbohydrate binding peptide can be the same or different lectin derived carbohydrate bindina peptide and the spacer arm is selected to provide for optimal distance to bind to the carbohydrate.

However, the invention is not restricted to the use of lectin derived carbohydrate binding peptides specifically exemplified in FIG. 1 or to multivalent derivatives thereof, but rather embraces the use of any lectin derived peptide or derivative thereof which binds terminally linked α-sialic acid(2→6) βGal- and/or α-sialic acid(2→3)βGal-carbohydrate structures. As noted previously, peptides capable of binding such structures, when administered to a mammal, result in the inhibition of immune responses and cellular interactions, in particular, inflammatory responses or conditions, tolerance to antigens, modulation of the immunogenic response to antigens, and the inhibition of cell adhesion events, which are involved, e.g., in metastasis and inflammation.

It is well within the level of ordinary skill to identify other lectin derived peptides capable of binding terminally linked α-sialic acid(2→6)βGal- and/or α-sialic acid(2→3)βGal-structures, by conventional methods for assaying binding between ligands. Such methods include, e.g., competitive binding assays and receptor binding assays. The subject application, in particular, sets forth one method in the examples which illustrates rather simple assaying techniques that are capable of determining binding to terminally linked α-sialic acid(2→6)βGal- and/or α-sialic acid(2→3) βGal-structures. Other methods for determining the binding of a candidate peptide with such terminally linked structures are known in the art. See, for example, Pearce-Pratt et al[31].

The subject invention accordingly further provides a method by which lectin derived peptides capable of inducing or suppressing various immune responses and cellular interactions, e.g., inflammation, antigenic tolerance, modulation of antigenic response, or cell adhesion, may be putatively identified on the basis of their ability to bind to terminally linked α-sialic acid(2→6)βGal- and/or α-sialic acid(2→3)βGal-structures.

In regard to the above, the subject invention contemplates the attachment of labels or label binding groups to the lectin derived carbohydrate binding peptides and/or to candidate lectin derived carbohydrate binding peptides in order to facilitate the assays described above. Such labels are conventionally formed on the peptides by methods well known in the art. Suitable labels include, by way of example, enzymes (e.g., horseradish peroxidase), radioisotopes (e.g., $^{125}$I), fluorescent moieties, chemiluminscent moieties, and the like.

Suitable label binding moieties are also well known in the art and include, by way of example, biotin, avidin, antibodies, etc. A preferred label binding moiety is biotin which permits binding of the peptide/biotin adduct to avidin. The avidin can be appropriately labeled so that resulting peptide/biotin/avidin complex can be detected.

The subject invention also contemplates kits for use in conducting such assays. Such kits would comprise the labelled lectin derived carbohydrate binding peptide or the lectin derived carbohydrate binding peptide attached to label binding groups.

Suitable lectin derived carbohydrate binding peptides for use herein are those which are capable of binding terminally linked α-sialic acid(2→6)βGal- and/or α-sialic acid(2→3) βGal-structures. However, an additional prerequisite of efficacious lectin derived carbohydrate binding peptides will include suitability for in vivo administration. In particular, the lectin derived carbohydrate binding peptide should not be toxic, and should be sufficiently soluble at the required dosages, which will typically range from about 0.5–50 mg/kg of body weight. In this regard, it is art recognized that the solubility of lectin derived carbohydrate binding peptides can be enhanced by attaching hydrophilic amino acid groups and can be reduced by attaching hydrophobic amino acid groups from the carboxyl terminal and/or amino terminal positions of the peptide.

The invention further contemplates fragments or derivatives of peptides capable of binding terminally linked α-sialic acid(2→6)βGal- and/or α-sialic acid(2→3)βGal- structures which peptides have been modified to render them non-toxic e.g., by chemical derivatization, mutagenesis, etc., while still retaining the ability to bind such terminally linked structures.

The subject invention provides, in particular, methods for suppressing cell-mediated immune responses in mammals including cell-mediated inflammatory responses or disorders by the administration of an effective amount of one or more lectin derived carbohydrate binding peptides capable of binding terminally linked α-sialic acid(2→6)βGal- and/or α-sialic acid(2→3)βGal-structures or molecules/cell surfaces comprising such structures.

The cell-mediated immune responses or disorders treatable by the subject invention include inflammatory immune reactions involving specific and non-specific defense systems. As discussed above, such conditions include antibody responses to antigens, such as viruses, allergens, delayed-type hypersensitivity, autoimmune disorders such as rheumatoid arthritis and lupus, post-ischemic leukocyte-mediated tissue damage (reperfusion injury), frost-bite injury or shock-acute leukocyte-mediated lung injury (e.g., acute respiratory distress syndrome), asthma, traumatic shock, septic shock, nephritis, and acute and chronic inflammation, including atopic dermatitis, psoriasis, and inflammatory bowel disease. Further, inflammatory disorders treatable by the subject invention may include platelet-mediated pathologies such as atherosclerosis and clotting disorders.

Inflammatory conditions of special interest include delayed type hypersensitivity reactions, reperfusion, and acute leukocyte-mediated lung injury (ARDS).

This invention provides a generic method by which cell-mediated immune responses such as cell-mediated inflammatory responses or disorders in mammals (e.g., humans) may be suppressed by the administration of an effective amount of one or more lectin derived carbohydrate binding peptides or fragments or derivatives thereof capable of binding terminally linked α-sialic acid(2→6)βGal- and/or α-sialic acid(2→3)βGal-structures or molecules/cell surfaces comprising such structures. In a preferred embodiment, the invention provides methods by which inflammatory responses or disorders may be treated or suppressed by the administration of an effective amount of one or more peptides selected from the group of peptides set forth in FIG. 1.

The subject invention further provides a general method for inhibiting immune responses and cell adhesion events in mammals by the administration of an effective amount of one or more lectin derived carbohydrate binding peptides or fragments or derivatives thereof capable of binding terminally linked α-sialic acid(2→6)βGal- and/or α-sialic acid (2→3)βGal-structures or molecules/cell surfaces comprising such structures. Such immune responses include cell mediated and humoral immune responses. As has been discussed, such immune responses include, in particular, inflammatory responses or inflammatory disorders.

The invention further provides methods for affecting the induction of immune responses to antigens comprising administering to a mammal an antigen in conjunction with one or more lectin derived carbohydrate binding peptides capable of binding terminally linked α-sialic acid(2→6) βGal- and/or α-sialic acid(2→3)βGal-structures or molecules/cell surfaces comprising such structures. For example, administration of an effective amount of the SPYGRC (amino acids 18–23 of SEQ ID NO:3) hexapeptide to a mammal with an antigen will modulate the induction of the immune response in the mammal to the antigen.

Accordingly, the subject lectin derived carbohydrate binding peptides may comprise applicability as immune modulators, which may be administered in conjunction with vaccines, artificial organs or tissue transplants, and allogeneic organ and tissue transplants as a means for modulating the immune response to foreign antigens comprised therein.

It has further been found that the subject lectin derived carbohydrate binding peptides capable of binding terminally linked α-sialic acid(2→6)βGal- and/or α-sialic acid(2→3) βGal-structures or molecules/cell surfaces comprising such structures, when administered in an effective amount to a mammal which has been immunized with a particular antigen, result in the induction of long term tolerance to said antigen. In this regard, administration is conducted after onset of the secondary immune response but at or prior to one-half the period required for maximal inflammation.

Figure 3:
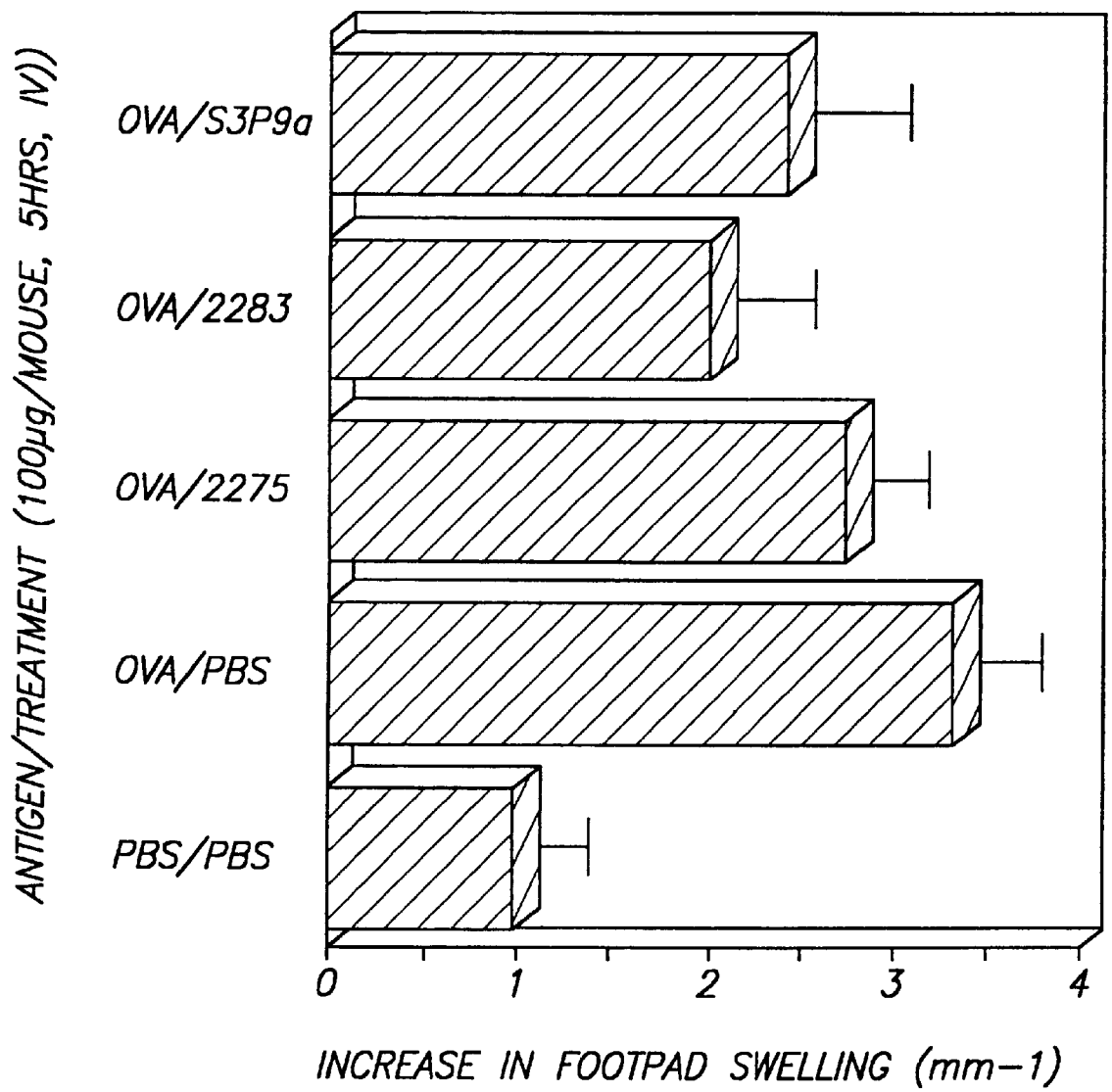
FIG. 3 illustrates the long term (2 week) effects on the DTH responses determined by footpad swelling, in groups of Balb/c mice which are immunized with 100 µg of the OVA antigen, challenged 7 days later with OVA, and then treated about 5 hours thereafter with a lectin derived carbohydrate binding peptide.

In particular, it has been found that administration, during the critical period set forth above, of an effective amount of the S3P9a (SEQ ID NO:9), the ACS2P1 (2275) (amino acids 9–23 of SEQ ID NO:3), and the SPYGRC (2283) (amino acids 18–23 of SEQ ID NO:3) peptides illustrated in FIG. 1 to mammals that have been immunized with an antigen, results in said mammals exhibiting a reduced immune response upon subsequent challenge(s) with said antigen (FIG. 3). Thus, the subject lectin derived carbohydrate binding peptides have applicability as tolerogens. Given this property, such lectin derived carbohydrate binding peptides or fragments or derivatives thereof may be especially suitable for use in the treatment of allergic disorders since administration of "tolerogenic" derivatized allergens is a known means for treating allergic disorders.

The subject invention further provides methods for inhibiting the adhesion of certain cell types [e.g., tumor cells and polymorphonuclear cells (PMN's)] to endothelial cells. In this regard, the art suggests that tumor metastasis involves tumor cell adhesion to selectin bearing cells. In this regard, circulating cancer cells apparently take advantage of the body's normal inflammatory mechanisms and bind to areas of blood vessel walls were the endothelium is activated and, accordingly, contains selecting. As noted previously, the putative receptors for such selectins contain terminally linked α-sialic acid(2→6)βGal- and/or α-sialic acid(2→3) βGal-structures. Therefore, administration of lectin derived carbohydrate binding peptides capable of binding terminally linked α-sialic acid(2→6)βGal- and/or α-sialic acid(2→3) βGal-structures should provide a method for inhibiting metastasis. For example, the subject lectin derived carbohydrate binding peptides or fragments or derivatives thereof may be administered before, during or after cancer surgery or biopsy as a means for inhibiting metastasis of tumor cells which may be released into the circulatory system during surgery. In these methods, the subject lectin derived carbohydrate binding peptides are administered either prior to, at the time of surgery or biopsy, or shortly thereafter. Prior administration is typically no more than about 5 hours prior to surgery or biopsy and administration and subsequent administration is typically no more than about 15 hours after surgery or biopsy. In either case, administration is either continuous or intermittent but preferably continuous.

In the methods pertaining to suppression of cell-mediated inflammatory reactions or disorders arising from injury or antigen exposure, the subject lectin derived carbohydrate binding peptides or fragments or derivatives thereof are administered after initiation of the mammals immune response but at or prior to one-half the period required for maximum inflammation to the antigen exposure or injury. Preferably, the subject lectin derived carbohydrate binding peptides are administered about 1–10 hours after initiation of the immune response, and more preferably about 1–5 hours after initiation of the immune response. However, the specific time for administration will vary dependent upon the particular antigen/injury and the lectin derived carbohydrate binding peptide which is administered.

In the methods pertaining to modulating the induction of an immune response to an antigen in a non-sensitized mammal, an effective amount of the subject lectin derived carbohydrate binding peptides or derivatives thereof will be administered in conjunction with the antigen. Typically, such conjunctive administration is simultaneous with antigen administration but can be up to ±3 hours from the time of antigen administration.

In the methods pertaining to induction of long term tolerance to an antigen, an effective amount of the subject lectin derived carbohydrate binding peptides or fragments or derivatives thereof will generally be administered after antigen challenge to a sensitized mammal. In particular, administration is after initiation of the mammal's secondary immune response to the antigen challenge but at or prior to one-half the period required for maximum inflammation to the antigen challenge. Preferably, the subject lectin derived carbohydrate binding peptides are administered about 1–10 hours after initiation of the immune response to the antigen challenge, and more preferably about 1–5 hours after initiation of the immune response to the antigen challenge. However, the specific time for administration will vary dependent upon the particular antigen and the lectin derived carbohydrate binding peptide which is administered.

Generally, the subject lectin derived carbohydrate binding peptides or derivatives thereof will be administered parenterally, e.g., by intramuscular or intravenous routes. However, other dosage forms should also be suitable including, e.g., oral, transdermal, rectal, intratracheal, and intranasal formulations. For example, intranasal and intratracheal formulations may be preferred if the inflammatory condition treated involves lung inflammation, e.g., acute respiratory distress syndrome (ARDS). In contrast, an oral formulation would likely be preferred if the inflammatory condition treated involves the digestive tract, e.g., inflammatory bowel disease.

Pharmaceutical compositions for use in the subject invention will generally comprise an effective amount of one or more of the subject peptides or derivatives thereof capable of binding terminally linked α-sialic acid(2→6)βGal- and/or α-sialic acid(2→3)βGal-structures in combination with a pharmaceutically acceptable carrier and/or excipients. The particular pharmaceutically acceptable carrier and excipients will vary dependent upon the dosage form. In one embodiment, several of the subject peptides or derivatives thereof are mixed into the pharmaceutical composition to form a "cocktail" having enhanced activity.

Parenteral dosage forms may contain phosphate buffered saline as a carrier, while intranasal formulations will comprise inhalants, and oral dosage forms may comprise enteric coatings. The selection of suitable carriers and excipients and formulation of different dosage forms is well within the level of ordinary skill in the pharmaceutical art.

As noted above, the subject lectin derived carbohydrate binding peptides or derivatives thereof are administered in effective amounts. An effective amount is an amount sufficient to obtain the desired therapy without causing undue toxicity to the mammal. Preferably, the subject peptides are administered at dosages ranging from about 0.5 to 50 mg/kg body weight, with 5–10 mg/kg being most preferred for each of the above cited methods. The specific dose employed is regulated by the particular cell-mediated immune response being treated as well as by the judgement of the attending clinician depending upon factors such as the severity of the adverse immune response, the age and general condition of the patient, and the like.

Generally, the methods of the present invention will involve administration of a single dose of the subject lectin derived carbohydrate binding peptides. However, the invention further contemplates repeated administration of the subject lectin derived carbohydrate binding peptides or derivatives thereof. Repeated administration of these peptides may be desirable, e.g., in the treatment of chronic or sustained inflammatory disorders, such as, rheumatoid arthritis, acute and chronic inflammation, psoriasis, inflammatory bowel disorders, and autoimmune disorders associated with inflammatory responses, such as lupus, multiple sclerosis or rheumatoid arthritis.

It is also contemplated that the subject peptides and derivatives are useful as receptor-targeted antibacterial and anti-viral drugs wherein the bacteria, virus, or toxin produced therefrom employs a terminally linked α-sialic acid (2→6)βGal- and/or α-sialic acid(2→3)βGal-structure as the receptor site on a cell of the targeted mammalian host.

Such bacteria/virus and/or toxins include, by way of example, influenza virus, pertussis toxin, cholera toxin, and the like. Such methods are illustrated in the examples hereinbelow wherein in vitro assays demonstrate the ability of two of the subject lectin derived carbohydrate binding peptides to neutralize the effects of pertussis toxin on Chinese Hamster Ovary cells.

Accordingly, when administered in effective amounts, the subject lectin derived carbohydrate binding peptides are useful in methods for inhibiting inoculation in mammalian hosts of bacterial/viral agents and/or their toxins which employ a terminally linked α-sialic acid(2→6)βGal- and/or α-sialic acid(2→3)βGal-structure as the receptor site on a cell of the targeted mammalian host thereby inhibiting the likelihood that the mammalian host will become afflicted with the disease produced by the bacterial/viral agent and/or its toxin.

Effective amounts of the subject lectin derived carbohydrate binding peptides or derivatives thereof will preferably be dosages ranging from about 0.5 to 50 mg/kg body weight, with 5–10 mg/kg being most preferred.

EXAMPLES

In order to fully illustrate the present invention and the advantages thereof, the following specific examples are given, it being understood that these examples are intended to be illustrative only and in nowise limitative of the scope of the present invention.

In these examples as well as in the application, all sugars disclosed herein are in their D form except for fucose which is in its L form and all amino acids are conventional.

In these examples, unless otherwise defined below, the abbreviations employed herein have their generally accepted meaning:

| | |
|---|---|
| ABTS = | 2,2'-azino-bis(3-ethylbenzathiazoline-6-sulfonic acid) |
| BSA = | Bovine serum albumin |
| cm = | centimeter |
| HPLC = | High Performance Liquid Chromatography |
| MAL = | Maackia amurensis |

-continued

| | |
|---|---|
| mg = | milligram |
| mM = | millimolar |
| mm = | millimeter |
| ng = | nanogram |
| nm = | nanometer |
| PBS = | phosphate buffered saline |
| PT = | Pertussis toxin |
| SNA = | Sambucus nigra |
| μg = | microgram |
| μl = | microliter |
| μM = | micromolar |
| μmol = | micromole |
| v/v = | volume/volume |

Unless otherwise indicated, all temperatures are in degrees Celsius (° C.). Also, as noted previously, all amino acid residues recited herein employ their conventional one letter abbreviation.

General Procedures

All of the reagents used in Examples 1–10 were obtained from Sigma Chemical Company, St. Louis, Mo., except for pertussis toxin (PT) which was obtained from Connaught Center for Biotechnology Research, Willowdale, Ontario, Canada; SNA-, WGA- and MAL-biotin, which were obtained from Boehringer Mannheim, Dorval, Quebec; and IODO-GEN which was from Pierce Chemical Co., St. Louis, Mo. The acetylated and biotinylated analogs of the peptide S2P1 (amino acids 9–23 of SEQ ID NO:3) were prepared using conventional methods. PT-biotin as well as asialo- and asialoagalactofetuin were prepared as described earlier[30,44]. Removable flat-bottomed microtiter well strips of Immunulon 2 were from Dynatech, Alexandria, Va.

Example 1

Synthesis of Synthetic Peptides

Peptides corresponding to amino acid sequences found in the S2 and S3 subunits of PT were synthesized using an ABI 403A peptide synthesizer (Applied Biosystems, Inc., Foster City, Calif.), then cleaved from the resin by HF and purified by reversed-phase HPLC on a Vydac C4 semipreparative column. All synthetic peptides used in ELISA inhibition assays were >95% pure as judged by analytical HPLC, and their amino acid analyses were in good agreement with the theoretical compositions.

Regions in the S2 and S3 subunits of PT that correspond to the variable amino acid sequences distinguishing the S2 from the S3 subunit were secured as above. These peptide sequences were chosen, in part, based on their high index of hydrophilic β-turns as judged by secondary structure prediction analysis[60,61]. Upon careful examination of the PT sequences, 20 peptides were synthesized including those containing amino acid residues 62–73 of WGA (SEQ ID NO:11). The acetylated version of S2P1 (amino acids 9–23 of SEQ ID NO:3) was also prepared in order to better mimic the native peptide backbone. The synthesized peptides are set forth in Table I below:

TABLE I

| Peptide | Position | Sequence* | SEQ ID NO |
|---|---|---|---|
| 1. S2P1 | 9–23 | PQEQITQHG SPYGRC | 3 (aa 9–23) |
| 2. ACS2P1-b | 9–23 | BIOTIN-PQEQITQHGSPYGRC-CO-NH$_2$ | 3 (aa 9–23) |
| 3. S2(14–23) | 14–23 | TQHGSPYGRC | 3 (aa 14–23) |
| 4. S2-b | 14–23 | BIOTIN-TQHGSPYGRC | 3 (aa 14–23) |
| 5. S2P2 | 1–23 | STPGIVIPPQEQITQHGSPYGRC | 3 |
| 6. SPYGRC | 18–23 | SPYGRC-CO-NH$_2$ | 3 (aa 18–23) |
| 7. SPYGRC-b | 18–23 | BIOTIN-SPYGRC-CO-NH$_2$ | 3 (aa 18–23) |
| 8. S2P3 | 78–98 | GAFDLKTTFCIMTTRNTGQPA | 4 |
| 9. S2P4 | 138–154 | YDGKYWSMYSRLRKMLY | 5 (aa 16–32) |
| 10. S2P6 | 123–154 | FVRSGQPVIGACTSPYDGKYW SMYSRLRKMLY | 5 |
| 11. S3P1 | 9–23 | PKALFTQQGGAYGRC | 6 (aa 9–23) |
| 12. S3P2 | 1–23 | VAPGIVIPPKALFTQQGGAYGRC | 6 |
| 13. S3P3 | 87–108 | CITTIYKTGQPAADHYYSKVTA | 7 (aa 10–31) |
| 14. S3P4 | 78–108 | AGFIYRETFCITTIYKTGQPAADHYYSKVTA | 7 |
| 15. S3P5 | 134–154 | CASPYEGRYRDMYDALRRLLY | 8 |
| 16. S3P9a | 110–127 | RLLASTNSRLCAVFVRDG | 9 |
| 17. S2(WGA)# | — | PQEQITQHGSQYGYC | 10 |
| 18. S2(WGA)-b | — | BIOTIN-PQEQITQHGSQYGYC | 10 |
| 19. WGA(62-73) | — | SQYGYCGFGAEY | 11 |
| 20. WGA(62-73)-b | — | BIOTIN-SQYGYCGFGAEY | 11 |

*Underlined sequences correspond to sequences found in the PT peptide that showed homology to the sequence SQYGHC (SEQ ID NO:12) found in the binding site of WGA isolectin 2 (24).
PT S2P1 sequence (amino acids 9–23 of SEQ ID NO:3) inserted with the WGA hexapeptide sequence (SQYGYC) (amino acids 10–15 of SEQ ID NO:10)
aa amino acid
b biotin The above peptides were tested for their ability to bind to terminally linked α-sialic acid(2→6)βGal- and α-sialic acid (2→3)βGal-structures in the examples below. In these examples, the peptides were first screened for their ability to inhibit binding of different lectins (PT, SNA, and MAL) known to bind to fetuin, a carbohydrate containing multiple copies of the αNeu5Ac(2→3)βGal(1→4)βGlc-structure.

Example 2

Binding Inhibition Assays (Initial Peptide Screening)

Microtiter wells were coated with 100 μl of fetuin or asialofetuin (50 μg/ml) in 50 mM sodium phosphate buffer (pH 6.8) containing 5 mM MgCl$_2$ and 15 MM NaN$_3$ for 16 hours at 4° C. The solution was removed by aspiration and replaced with 100 μl of 1% BSA in PBS containing 0.05% Tween 20 (PBST). After incubation for 2–4 hours at room temperature, the microtiter wells were washed four times with 300 μl of PBST. Peptides ranging in concentration from 0.5 to 4.5 mg/ml in PBS (40 μl) were added to each well and PT-biotin (10 μl containing 10 ng in PBS) was then added to the microtiter wells. After incubating for 1 hour, the binding reaction was stopped by aspirating the solutions and the plate was washed with PBST (300 μl). Horseradish peroxidase-conjugated avidin (100 μl, 1/3000 dilution in PBST to a concentration of 0.3 μg/ml) was then added to the wells, and the plates were incubated at ambient temperature for 1 hour. After washing the wells as described above, the substrate solution [1 mM ABTS in 5 mM citrate buffer, pH 4.2, containing 0.1% hydrogen peroxide, v/v) was added and the plates were incubated for 30 minutes. Color development was recorded at 405 nm using a Titertek Multiskan MC plate reader. Maximum binding was determined in the absence of peptide, and background binding was measured in wells coated with BSA only. Binding assays for each peptide were done in duplicate. Binding inhibition experiments utilizing SNA-, WGA-, and MAL-biotin were performed as described above using 10 ng of each biotinylated lectin in PBS.

The panel of 20 peptides were assayed for the ability to inhibit PT-, WGA-, MAL-, and SNA-biotin binding to fetuin or asialofetuin. The biotinylated plant lectins have proved to be useful controls, since we have previously showed that these lectins possess similar binding specificities as PT[25,46]. The results from this example are set forth in Table 2 below. These results indicate that peptides S2P3 (SEQ ID NO:4) and S2P6 (SEQ ID NO:5) inhibited PT biotin binding by 15–20% both to fetuin as well as asialofetuin. Two additional peptides derived from the S3 subunit (S3P3 (amino acids 10–31 of SEQ ID NO:7) and S3P5(SEQ ID NO:8)) were found to reduce binding of PT to asialofetuin only. The majority of the other peptides displayed in Table 2 exhibited either marginal inhibition or enhancement in binding of biotinylated PT to fetuin or asialofetuin. Peptides S2P1 (amino acids 9–23 of SEQ ID NO:3), ACS2P1 (amino acids 9–23 of SEQ ID NO:3) and S2P2 (SEQ ID NO:3) showed nearly a 2-fold enhancement of PT-biotin binding relative to control experiments done in the absence of peptide.

Peptide S2P3 (SEQ ID NO:4) was found to inhibit binding to fetuin of all the biotinylated lectins. However, it is noted that peptides S2P1 (amino acids 9–23 of SEQ ID NO:3) and S2P2 (SEQ ID NO:3), which showed enhancement of binding of PT to fetuin, inhibited WGA binding activity.

III). The two peptide sequences from the S3 subunit (S3P3 (amino acids 10–31 of SEQ ID NO:7) and S3P5 SEQ ID NO:8)) were found to inhibit PT-biotin's interaction with asialofetuin in a concentration-dependent manner, but their $IC_{50}$ values are above the solubility limits of the peptide in PBS. The peptide S2P3 (SEQ ID NO:4) was also very active at inhibiting the interaction of MAL- and WGA-biotin with fetuin. Upon closer examination this peptide proved to be non-inhibitory for SNA-biotin. Two additional peptides from S2 (S2P1 (amino acids 9–23 of SEQ ID NO:3) and S2P2 (SEQ ID NO:3)) were active at inhibiting WGA-biotin binding at millimolar concentrations, suggesting that these peptide sequences may also be important for interacting with oligosaccharide in the binding site of WGA.

TABLE II

Percent Changes in Binding Activity

| Peptide | SEQ ID NO | Concentration (mg/mL) | PT/ fetuin* | MAL/ fetuin | SNA/ fetuin | WGA/ fetuin | PT/ asialio-fetuin |
|---|---|---|---|---|---|---|---|
| S2P1 | 3 (aa 9–23) | 1.2 | +85 ± 4 | +8 ± 4 | −5 ± 1 | −18 ± 2 | +113(1) |
| ACS2P1 | 3 (aa 9–23) | 1.0 | +89 ± 3 | +16 ± 9 | −3 ± 1 | −22 ± 6 | +190 ± 23 |
| S2 (14–23) | 3 (aa 14–23) | 1.0 | +68 ± 9 | +32 ± 1 | +1 ± 2 | +7 ± 1 | ND |
| S2P2 | 3 | 1.1 | +58 ± 4 | +14 ± 2 | −1 ± 1 | −15 ± 2 | +33(1) |
| S2P3 | 4 | 0.51 | −21 ± 0 | −18 ± 2 | −15 ± 4 | −56 ± 8 | −15(1) |
| S2P4 | 5 (aa 16–32) | 0.98 | +14 ± 22 | +2(1) | +3(1) | +15 ± 1 | −3(1) |
| S2P6 | 5 | 0.85 | −28 ± 6 | +18 ± 16 | +2 ± 2 | +57 ± 0 | −18(1) |
| S3P1 | 6 (aa 9–23) | 3.2 | +54 ± 25 | +4 ± 6 | −2 ± 1 | −9 ± 4 | +45 ± 16 |
| S3P2 | 6 | 3.1 | +77 ± 59 | +12 ± 16 | +3 ± 3 | +9 ± 4 | +82 ± 11 |
| S3P3 | 7 (aa 10–31) | 4.5 | +19 ± 67 | +13 ± 15 | +3 ± 0 | +6 ± 3 | −28 ± 7 |
| S3P4 | 7 | 3.3 | +12 ± 2 | +7 ± 1 | +1(1) | +13 ± 1 | +75 ± 50 |
| S3P5 | 8 | 0.48 | +14 ± 6 | +3 ± 6 | 0(1) | +35 ± 8 | −26 ± 10 |
| S3P9a | 9 | 1.7 | +328 ± 10 | +18 ± 6 | −41 ± 3 | ND | ND |
| SPYGRC | 3 (aa 18–23) | 4.4 | +34 ± 2 | −16 ± 0 | −2 ± 2 | +7 ± 3 | +7 ± 9 |
| S2(WGA) | 10 | 1.0 | +79 ± 15 | +22 ± 3 | 0 ± 1 | −4 ± 3 | ND |
| WGA (62–73) | 11 | 1.0 | −32 ± 5 | −1 ± 4 | −3 ± 2 | −9 ± 1 | ND |

*Biotinylated lectin/glycoprotein bound to microtiter wells. Positive signs preceding the numbers in this table indicate enhancement and negative signs indicate inhibition of binding.
(1) One determination only.
aa amino acid
ND Not determined.

Example 3

Binding Inhibition Assays (Determination of IC 50 Values)

Peptides found to have inhibitory activity in the initial screening experiments were further analyzed in binding inhibition experiments to determine the concentration of peptide that was required to reduce binding by 50% ($IC_{50}$ values).

Inhibition experiments were performed by a method similar to that described in Example 2 with 2-fold dilutions of PT peptide in PBS, except that microtiter wells were coated with 3 μg/ml fetuin or asialofetuin. Binding assays for each inhibitor concentration were done at least in duplicate, and the average value varied less than 15%. The concentration of peptide required for 50% inhibition ($IC_{50}$) was determined by plotting the amount of binding observed in the presence of peptide inhibitor as a percent of the maximum binding achieved without inhibitor.

Two of the peptides derived from the S2 subunit were able to inhibit PT-biotin binding to fetuin at submillimolar concentrations, but they were unable to inhibit PT-biotin binding to asialofetuin in subsequent experiments (Table

TABLE III

Concentrations of PT Peptides and WGA Peptides Resulting in 50% Inhibition of Biotinylated PT and Lectins Binding to Fetuin or Asialofetuin

| Biotinylated Lectin (glycoprotein) | Peptide | SEQ ID NO | $IC_{50}$(mM) |
|---|---|---|---|
| PT-b (fetuin) | S2P3 | 4 | 0.19 ± 0.09 |
| PT-b (fetuin) | S2P6 | 5 | 0.22 ± 0.06 |
| WGA-b (fetuin) | ACS2P1 | 3 (aa 9–23) | 3.25 ± 0.45* |
| WGA-b (fetuin) | S2P2 | 3 | SI |
| WGA-b (fetuin) | S2P3 | 4 | 0.14 ± 0.03 |
| MAL-b (fetuin) | S2P3 | 4 | 0.86 ± 0.02 |
| PT-b (asialofetuin) | S3P3 | 7 (aa 10–31) | SI |
| PT-b (asialofetuin) | S3P5 | 8 | SI |
| SNA-b (fetuin) | S3P9a | 9 | 2.74 ± 0.86 |
| PT-b (fetuin) | WGA(62–73) | 11 | 1.5 ± 0 |
| WGA-b (fetuin) | WGA(62-73) | 11 | 3.4 ± 0 |

SI Slightly inhibitory, but the concentration of peptide required for 50% inhibition of binding is above the solubility limit of the peptide
*Unacetylated form of S2P1 (amino acids 9–23 of SEQ ID NO: 3) inhibited to the same extent as the acetylated form.
aa amino acid--;

Since three of the peptides derived from the S2 subunit of PT were able to inhibit WGA binding, the amino acid sequences which constitute the sialic acid binding site of WGA were closely examined to determine if there were any homologies with the inhibitory PT S2 peptide sequences. One short 6-amino acid sequence (SQYGHC) corresponding to amino acids 62–67 in WGA isolectin 2 displayed reasonable homology with a sequence found both in the S2P1 (amino acids 9–23 of SEQ ID NO:3) and S2P2 (SEQ ID NO:3) peptides (SPYGRC, amino acids 18–23 of SEQ ID NO:3) from PT. This short sequence in WGA is responsible for binding with the carbonyl of the N-acetyl group of sialic acid or N-acetyl-glucosamine (i.e. serine 62) through a hydrogen bond. Non-polar interactions between the aromatic side chains of tyrosine 64 as well as histidine 66 interact with the glycerol side chain of sialic acid and the pyranose ring of sialic acid or N-acetyl-glucosamine, respectively[62]. The other inhibitory peptide, S2P3 (SEQ ID NO:4), did not display any good homology with sequences responsible for interacting with sialic acid in WGA. This indicates that other motifs may also be functionally important for interaction with sialic acid.

Example 4

Binding Inhibition Studies Utilizing Biotinylated and Acetylated S2P1 (amino acids 9–23 of SEQ ID NO:3)

From the initial peptide screening results (Table II), peptides S2P1 (amino acids 9–23 of SEQ ID NO:3) and S2P2 (SEQ ID NO:3) showed a 2-fold enhancement in binding of PT-biotin to fetuin relative to control experiments. One possible explanation for the enhancement may be the ability of the peptide to form a bridge between PT-biotin and fetuin. In order for the peptide to act as a bridging molecule, the peptide must contain both a recognition site for fetuin as well as a sequence which binds to PT itself. To answer this question an acetylated and biotinylated form of the peptide S2P1 (amino acids 9–23 of SEQ ID NO:3) (biotinylated at the terminal proline) was prepared to determine if we could measure direct binding of the peptide to PT and fetuin.

Binding assays were done as described in Example 2 in PBS by using ACS2P1-biotin (amino acids 9–23 of SEQ ID NO:3) at a concentration of 10 μg/ml in PBS. Assays were carried out for 1 hour at room temperature and the amount of biotinylated peptide bound to fetuin, determined by using avidin-peroxidase.

From these direct binding studies, a concentration-dependent binding both to fetuin as well as to PT immobilized in microtiter wells was observed. Furthermore, the binding of ACS2P1-biotin (amino acids 9–23 of SEQ ID NO:3) to PT could be inhibited by fetuin ($IC_{50}$=50 μM; n=2) indicating that the biotinylated peptide bound at or adjacent to the fetuin binding site in PT.

In view of the above, it was concluded that because of potential bridging by the peptide between the lectin and the fetuin, any of the peptide sequences set forth in Table I which caused reduction in the binding of any of the lectins to fetuin were able to bind to terminally linked α-sialic acid(2→6)βGal- and α-sialic acid(2→3)βGal-structures.

Example 5

Binding Inhibition Assays Using Oligosaccharides to Inhibit the Binding of ACS2P1-biotin (Amino Acids 9–23 of SEQ ID NO:3)

The binding results obtained for ACS2P1-biotin (amino acids 9–23 of SEQ ID NO:3) described in Example 4 above indicate a direct involvement of carbohydrate moiety with the lectin through a biotinylated peptide bridge.

In order to assess the binding to α-sialic acid(2→6)βGal- and α-sialic acid(2→3)βGal-structures by this peptide as well as the hexapeptide SPYGRC (amino acids 18–23 of SEQ ID NO:3) which only exhibited reduction in the binding of one lectin to fetuin (Table II), inhibition experiments with simple saccharides were conducted to determine if the interaction was carbohydrate-dependent. The simple sugars chosen were sialic acid, sialyllactose from bovine colostrum (contains a mixture of α(2→6) and α(2→3) linked sialic acid structures), lactose, and N-acetyl-glucosamine.

Binding inhibition assays were done using sialic acid, sialyllactose, lactose, or N-acetyl-glucosamine at a concentration of 8 mM in PBS. Inhibition assays were done for 1 hour as described above (e.g., Example 2) at room temperature and the amount of biotinylated peptide bound to fetuin (3 μg/ml) quantitated by using avidin-peroxidase. The pH of free sialic acid was carefully monitored and adjusted to physiological pH values with dilute sodium hydroxide. The results of this example are set forth in Table IV below:

TABLE IV

Inhibition of Binding of ACS2P1-biotin (amino acids 9–23 of SEQ ID NO: 3) and SPYGRC-biotin (amino acids 18–23 of SEQ ID NO: 3) to Fetuin by Simple Saccharides*

| | Percent Changes in Binding Activity | |
| --- | --- | --- |
| Saccharide | ACS2P1-biotin (amino acids 9–23 of SEQ ID NO:3) (n = 3) | SPYGRC-biotin (amino acids 18–23 of SEQ ID NO:3) (n = 3) |
| Sialic acid | −19 ± 6 | +9 ± 8 |
| Sialyllactose | −46 ± 3 | −24 ± 6 |
| Lactose | +74 ± 7 | +20 ± 11 |
| N-Acetylglucosamine | −10 ± 2 | +6 ± 5 |
| Sucrose | 0 ± 3 | ND |

*Inhibition experiments were carried out as outlined above using 0.1 μg or 0.5 μg of ACS2P1-biotin (amino acids 9–23 of SEQ ID NO:3) and SPYGRC-biotin amino acids 18–23 of SEQ ID NO:3) respectively. Positive signs preceding the number in this table indicate enhancement and negative signs indicate inhibition of binding to fetuin.
ND Not determined The above results indicate that both peptides tested were able to bind to terminally linked α-sialic acid(2→6)βGal- and α-sialic acid(2→3)βGal-structures. Control experiments indicated that sialic acid was necessary for high affinity interaction since lactose failed to reduce the binding of ACS2P1-biotin (amino acids 9–23 of SEQ ID NO:3). N-acetyl-glucosamine was also found to marginally inhibit the binding of biotinylated peptide (10±2%, n=3) suggesting that the ACS2P1-biotin (amino acids 9–23 of SEQ ID NO:3) may have weak affinity for the N-acetylglucosamine consistent with the finding described below, which shows enhanced binding of the peptide to asialoagalactofetuin relative to asialofetuin. This is also in good agreement with previous results, which indicate PT's binding specificities to be similar to those of WGA[44,52].

In view of the above, it was concluded that any of the peptides which inhibit the binding of fetuin to any of the lectins set forth in Table II above are effective in binding to terminally linked α-sialic acid(2→6)βGal- and α-sialic acid (2→3)βGal-structures. Such peptides are set forth in FIG. 1.

Example 6

Screening of S2 and S3 Peptides from PT for the Ability to Inhibit ACS2P1-biotin (Amino Acids 9–23 of SEQ ID NO:3) Binding to Fetuin and Asialofetuin Binding inhibition assays were conducted using S2 and S3 peptides from PT in PBS as competitors for binding of ACS2P1-biotin (amino acids 9–23 of SEQ ID NO:3) (10 μg/ml) to fetuin or asialofetuin. Inhibition assays were done for 1 hour at room temperature, as described above, and the amount of biotinylated peptide bound to fetuin or asialofetuin (3 μg/ml) quantitated by using avidin-peroxidase.

The specificity and relative affinity of ACS2P1-biotin (amino acids 9–23 of SEQ ID NO:3) for fetuin was determined by performing binding inhibition experiments with the peptides shown in Table I. Binding inhibition experiments (Table V) indicated that the ACS2P1 peptide (amino acids 9–23 of SEQ ID NO:3) bound to fetuin with high affinity ($IC_{50}$=4.1 μM; n=2) when the unbiotinylated form of ACS2P1(amino acids 9–23 of SEQ ID NO:3) was used as competitor. The peptide S2P2 (SEQ ID NO:3), an extended version of S2P1 (amino acids 9–23 of SEQ ID NO:3) was also found to inhibit ACS2P1-biotin (amino acids 9–23 of SEQ ID NO:3) binding to fetuin but with a 10-fold decrease in affinity ($IC_{50}$=42.5 μM). Both peptides were unable to compete for the binding of ACS2P1-biotin (amino acids 9–23 of SEQ ID NO:3) to asialofetuin, indicating the importance of sialic acid for high affinity interaction with the peptide. Similar hexapeptide sequences to those found within the S2P1 (amino acids 9–23 of SEQ ID NO:3) and S2P2 (SEQ ID NO:3) peptides are also present in a number of the peptides from Table I (see underlined segments). Each of these peptides were analyzed for their ability to inhibit ACS2P1-biotin (amino acids 9–23 of SEQ ID NO:3) binding to fetuin and asialofetuin at peptide concentrations 10-fold higher than the $IC_{50}$ determined for the S2P1 (amino acids 9–23 of SEQ ID NO:3) peptide. None of the other peptides examined from Table I had the ability to inhibit binding of ACS2P1-biotin (amino acids 9–23 of SEQ ID NO:3) to fetuin or asialofetuin to the same extent indicating that the peptide sequence SPYGRC (amino acids 18–23 of SEQ ID NO:3) may play a crucial role for binding sialic acid. This is further confirmed by the inability of the peptides S3P1 (amino acids 9–23 of SEQ ID NO:6) and S3P2 (SEQ ID NO:6), which possess the strongest homologies to the sequence found in S2P1 (amino acids 9–23 of SEQ ID NO:3), to inhibit binding even at high concentrations of peptide. The homologous sequence found in the S3 peptides (GAYGRC) (amino acids 18–23 of SEQ ID NO:6) lacks the serine amino acid residue, which was shown to be important for forming an important hydrogen bond with the carbonyl of the N-acetyl group in the sialic acid binding site of WGA[62]. This indicates that the serine residue found in the S2P1 (amino acids 9–23 of SEQ ID NO:3) peptide may function in an analogous manner in the binding of S2P1 (amino acids 9–23 of SEQ ID NO:3) to sialic acid.

The results of this example are set forth in Table V below:

TABLE V

Screening of S2 and S3 Peptides from PT for the Ability to Inhibit ACS2P1-biotin (amino acids 9–23 of SEQ ID NO:3) Binding

| Peptide | SEQ ID NO | Concentration (μM) | Fetuin[1] | Asialofetuin[1] |
|---|---|---|---|---|
| ACS2P1 | 3 (aa 9–23) | 4.1 | −50 | +101 ± 2 |
| S2P2 | 3 | 42.5 | −50 | +6 ± 1 |
| SPYGRC | 3 (aa 18–23) | 5520 | −24 ± 2 | −54 ± 3 |
| S2P3 | 4 | 22.4 | +70 ± 11 | +15 ± 11 |
| S2P4 | 5 (aa 16–23) | 6.0 | −8 ± 16 | +2 ± 4 |
| S2P6 | 5 | 319 | +49 ± 5 | +18 ± 16 |
| S3P1 | 6 (aa 9–23) | 1142 | +245 ± 28 | +4 ± 0 |
| S3P2 | 6 | 934 | +88 ± 72 | +12 ± 16 |
| S3P3 | 7 (aa 10–31) | 16.1 | −13 ± 16 | −10 ± 11 |
| S3P4 | 7 | 6.4 | +55 ± 26 | +26 ± 2 |
| S3P5 | 8 | 22.5 | −19 ± 4 | −17 ± 8 |

The effect of S2 and S3 PT peptides on the binding of ACSP1-biotin (amino acids 9–23 of SEQ ID NO:3) (0.1 μg) to feutin or asiolofetuin. Negative and positive values refer to percent inhibition or enhancement respectively.
aa amino acid
[1]Percent Change in Binding Activity

Example 7

Iodination of ACS2P1-biotin (Amino Acids 9–23 of SEQ ID NO:3)

Previous reports have suggested the importance of tyrosine amino acid residues in the binding of PT to sialylated glycoprotein receptors44,63. These reports were based on the observation that if PT is iodinated by the conventional IODO-GEN procedure (selectively modifies tyrosine residues) without first protecting the binding site for fetuin, the binding activity of PT was reduced.

To determine if the tyrosine residue found in ACS2P1-biotin (amino acids 9–23 of SEQ ID NO:3) plays a role in the binding activity, the peptide was iodinated by the IODO-GEN procedure and its binding activity compared with the uniodinated peptide. Specifically, ACS2P1-biotin (amino acids 9–23 of SEQ ID NO:3) (100 μg 0.052 μmol) in 100 μl of PBS was placed in a 12×75-mm glass tube coated with IODO-GEN, and 0.1 mM solution of NaI (50 μL 5 μmol) was added and gently mixed over a period of 10 minutes at room temperature. The reaction was terminated by removing the mixture from the IODO-GEN tube and the iodinated peptide was purified on a Sephadex G-25 column (1×15 cm equilibrated with PBS). Individual fractions were analyzed for the presence of peptide by measuring absorbance at 220 nm, and the concentration was determined by comparing the absorbance with underivatized ACS2P1-biotin (amino acids 9–23 of SEQ ID NO:3). A sample of iodinated and underivatized ACS2P1-biotin (amino acids 9–23 of SEQ ID NO:3) were diluted to a concentration of 10 μg/ml and analyzed for binding to fetuin coated microtiter wells as described in Example 6. In addition, binding of ACS2P1-biotin (amino acids 9–23 of SEQ ID NO:3) (10 μg/ml) to fetuin, asialofetuin, and asialoagalactofetuin (each at 3 μg/ml) was done in a similar manner.

The results of this experiment indicate that extensive iodination of ACS2P1-biotin (amino acids 9–23 of SEQ ID NO:3) reduced binding of the peptide to fetuin by 58±3% (n=3), which suggests the importance of the tyrosine amino acid in addition to the serine for the binding activity of ACS2P1-biotin (amino acids 9–23 of SEQ ID NO:3) to terminally linked α-sialic acid(2→6)βGal- and α-sialic acid (2→3)βGal-structures.

To determine whether the amino acid sequence in the S2 subunit of PT that corresponds to the peptide S2P1 (amino acids 9–23 of SEQ ID NO:3) plays an actual role in the lectin-like binding activity of PT, the binding specificity of the biotinylated peptide was compared with that of PT using fetuin, asialofetuin, and asialoagalactofetuin. A previous report had determined that the binding of $^{125}$I-PT to asialofetuin was 53±7%, while asialoagalactofetuin was 81±8% relative to control binding to fetuin[44]. This is in good agreement with the results obtained with ACS2P1-biotin (amino acids 9–23 of SEQ ID NO:3) which showed 45±9% and 93±18% (n=3) binding to asialo- and asialoagalactofetuin, respectively, relative to fetuin. These results suggest that this amino acid sequence may contain a portion of a lectin-like binding site in the S2 subunit of PT, which is responsible for the binding results previously observed.

Example 8

Binding assays were carried out essentially as described above using microtiter wells that were coated with 50 μl of BSA glycoconjugate (50 μg/ml) in 50 mM sodium phosphate buffer (pH 6.8) containing 5 mM MgCl$_2$ nd 15 mM NaN$_3$ for 16 hours at 4° C. The solution was removed by aspiration and replaced with 100 μl of 1% BSA in PBS containing 0.05% Tween 20 (PBST) and incubated at room temperature for an additional 2–3 hours. The microtiter wells were washed four times with 300 μl of PBST and then replaced with ACS2P1-biotin (amino acids 9–23 of SEQ ID NO:3) (0.1 μg) or SPYGRC-biotin (0.5 μg) in 50 μl of PBS. After incubating for 1 hour, the binding reaction was stopped by aspirating the solutions and the plate was washed with PBST (4×300 μl). Avidin-peroxidase (100 μl of a 1/3000 dilution of a 1 mg/ml solution in PBST) was added and incubated for an additional 1 hour. After washing the wells as described above, the substrate solution (1 mM ABTS in 5 mM citrate buffer, pH 4.2, containing 0.1% hydrogen peroxide, v/v) was added and the plates were incubated for 30 minutes. Binding assays for each BSA conjugate were done in triplicate and background binding was measured in wells coated with BSA only. The extent of biotinylated peptide binding is expressed as a percentage relative to fetuin as shown in Table VI below:

TABLE VI

Binding of ACS2P1-biotin (amino acids 9–23 of SEQ ID NO:3) and SPYGRC-biotin (amino acids 18–23 of SEQ ID NO:3) to BSA Conjugates*

| Carbohydrate Structure of BSA Conjugate | % Binding Relative to Fetuin of ACS2P1-b (amino acids 9–23 of SEQ ID NO:3) (n = 3) | % Binding Relative to Fetuin of SPYGRC-b (amino acids 18–23 of SEQ ID NO:3) (n = 3) | Common Name for Carbohydrate Structure |
|---|---|---|---|
| αNeuAc(2–3)βGal(1–4)βGlcNAc-BSA | 117 ± 12 | 120 ± 7 | SLacNAc |
| αNeuAc(2–3)βGal(1–3)βGlcNAc-BSA | 70 ± 4 | 97 ± 12 | SLe$^c$ |
| αNeuAc(2–6)βGal(1–4)βGlcNAc-BSA | 94 ± 2 | 122 ± 5 | SLacNAc |

TABLE VI-continued

Binding of ACS2P1-biotin (amino acids 9–23 of SEQ ID NO:3) and SPYGRC-biotin (amino acids 18–23 of SEQ ID NO:3) to BSA Conjugates*

| Carbohydrate Structure of BSA Conjugate | % Binding Relative to Fetuin of ACS2P1-b (amino acids 9–23 of SEQ ID NO:3) (n = 3) | % Binding Relative to Fetuin of SPYGRC-b (amino acids 18–23 of SEQ ID NO:3) (n = 3) | Common Name for Carbohydrate Structure |
|---|---|---|---|
| αNeuAc(2–3)βGal(1–4)βGlcNAc-BSA (1–3)αFuc | 84 ± 3 | 120 ± 4 | SLe$^x$ |
| αNeuAc(2–3)βGal(1–3)βGlcNAc-BSA 1–4)αFuc | 84 ± 14 | 103 ± 8 | SLe*(C19.9) |

*Experiments were done by coating 50 μg/mL BSA-conjugate or fetuin and probed with 0.1 μg ACS2P1-biotin (amino acids 9–23 of SEQ ID NO:3) of SPYGRYC-b (amino acids 18–23 of SEQ ID NO:3) for 1 hour at room temperature.

Example 9

Formation of a SPYGRC-Streptavidin-Biotin (Amino Acids 18–23 of SEQ ID NO:3) Conjugate Streptavidin (50 μg) in PBS was combined with SPYGRC-biotin (amino acids 18–23 of SEQ ID NO:3) (50 μl, 200 μg) and PBS (150 μl) and mixed for 1 hour at room temperature. The reaction mixture was loaded onto a Sephadex G-25 column (1×15 cm that had been equilibrated in PBS) and fractions collected. Protein containing fractions were analyzed by SDS PAGE gel electrophoresis and the molecular weight was determined. The results were consistent with the formation of a tetravalent complex between peptide and streptavidin. Lectin binding inhibition experiments were carried out as described previously for determination of IC$_{50}$'s. The results are set forth in Table VII below:

TABLE VII

The Effect of the Peptide SPYGRC or SPYGRC-biotin-Streptavidin (amino acids 18–23 of SEQ ID NO:3) Conjugate on the Binding of Biotinylated PT and Lectins to Fetuin*

| Biotinylated lectin | Concentration of SPYGRC Peptide (amino 18–23 of SEQ ID NO:3) (mg/ml) | % Changes in Binding Activity | Concentration of Peptide-Streptavidin Conjugate (μg/ml) | % Changes in Binding Activity |
|---|---|---|---|---|
| PT-b | 4.4 | +34 ± 2 | 500 | +13 ± 11 |
| MAL-b | 4.4 | −16 ± 0 | 1.0 | −50 ± 3 |
| SNA-b | 4.4 | −2 ± 1 | 1.2 | −50 ± 5 |
| WGA-b | 4.4 | +7 + 3 | 64 | −50 ± 1 |

*Positive signs preceding the numbers in this table indicated enhancement and negative signs indicate inhibition of binding.

Example 10

Neutralization of Pertussis Toxin Binding to Chinese Hamster Ovary (CHO) Cell by Synthetic Peptides Confluent monolayers of CHO cells were lifted from plastic tissue culture flasks with 0.25% trypsin and suspended at a concentration of 5×10⁴ cells/ml in Ham's F12 media containing 10% fetal bovine serum (FBS). 100 µl of the cell suspension was added to 96 well tissue culture plates and were allowed to establish contact with the plastic for 24 to 48 hours. The expended media was then removed and filtered-sterilized peptide 5-fold dilutions ranging in concentration from 300 to 30 femptogram per ml (80 µl) in Ham' F12 media containing FBS were added to the CHO cells. 20 µl of a PT solution (final PT concentration 2.7 ng/ml) was then added to the tissue culture wells contain peptide. The incubation mixtures were gently mixed and incubated at 37° C. for 1 hour in a $CO_2$ incubator. The incubation mixtures were then removed and replaced with fresh media. The tissue culture plates were then incubated for 24 hours at 37° C., fixed with 100% methanol, and stained with Geimsa stain. Control experiments were done in the absence of peptide alone or in the absence of PT. All determinations were done in triplicate. Stained CHO cells were then examined for inhibition of characteristic CHO cell clumping which is mediated by pertussis toxin binding and scored as to whether there was greater than 50% inhibition of clumping of CHO cells relative to control wells in the presence of PT only. The results reported in Table VIII show the maximum peptide concentration required to cause a 50% reduction in CHO cell clumping.

TABLE VIII

CHO Cell Neutralization Experiments Using PT S2 and S3 Peptides*

| PT Peptide | SEQ ID NO | Maximal Inhibitory Concentration for Greater than 50% Inhibition |
|---|---|---|
| ACS2P1 | 3 (aa 9–23) | 96 pg/ml |
| SPYGRC | 3 (aa 18–23) | 480 pg/ml |
| S2P2 | 3 | NI |
| S3P1 | 6 (aa 9–23) | NI |
| S3P2 | 6 | NI |
| S3P9a | 9 | NI |

*CHO cell neutralization experiments were carried out using a PT concentration of 2.4 ng/ml. CHO cell (5.4 × 10⁴ cells/ml) were exposed to incubation mixtures containing peptide and PT for 1 hour at room temperature. Control experiments were done in the absence of peptide.
aa amino acid
NI Not inhibitory at a peptide concentration of 300 ng/ml.
pg pgicogram The above data demonstrates that at least certain of the subject peptides would be effective in inhibiting the attachment of bacterial/viral agents and/or their toxins which utilize α-sialic acid(2→6)βGal- and/or α-sialic acid(2→3) βGal-structures as the attachment point on the surface of mammalian cells. Such agents/toxins include known toxins such as pertussis toxin, cholera toxin, etc. and, accordingly, administration of an effective amount of at least one of the subject peptides to a mammal would be effective in inhibiting such attachment.

Examples 11 and 12 below illustrate in vivo results for the subject peptides.

Example 11

Inhibition of DTH Inflammatory Response

DTH inflammatory responses -were measured using the mouse footpad swelling assay as described by Smith and Ziola[64]. Briefly, groups of Balb/c mice (about 19–20 grams each) were immunized with 100 µg of the OVA antigen containing 20 µg of the adjuvant (DDA—dimethyl-dioctadecylammonium bromide) which also induces a strong inflammatory DTH response. Seven days later, each group of mice was footpad-challenged with 20 µg of the OVA antigen (without adjuvant). The resulting inflammatory footpad swelling was measured with a Mitutoyo Engineering micrometer 24 hours after challenge.

To assess the effect of different peptidds on the inflammatory DTH response, groups of mice received 100 µg of the following peptides: ACS2P1 (2275) (amino acids 9–23 of SEQ ID NO:3), SPYGRC (2283) (amino acids 18–23 of SEQ ID NO:3), and S3P9a (SEQ ID NO:9). These peptides were injected as a solution into the tail vein, 5 hours after challenge. Control groups were left untreated or received 100 µL of phosphate-buffered saline (PBS). The results of this experiment are shown in FIG. 2 which illustrates that the peptides employed were effective in reducing a DTH response in mice.

Example 12

Persistence of Suppression of the DTH Inflammatory Response at 2 Weeks After Challenge Identical groups of mice treated with the peptides in Example 11 above, were re-challenged with OVA antigen 2 weeks after primary immunization. Untreated controls responded with the usual degree of footpad swelling whereas all other groups showed reduced footpad swelling. Specifically, these results are set forth in FIG. 3 which illustrates reduction in the degree of footpad swelling in mice previously treated with the subject peptides.

In addition to providing suppression of antigen induced inflammation in a sensitized mouse, the above data demonstrate that treatment with the subject peptides as per this invention also imparts tolerance to still later challenges from the same antigen.

In view of the fact that the immune system of mice serves as a good model for the immune system of humans, the above data demonstrates that the subject peptides would be effective in suppressing cell-mediated immune responses in humans and, when the cell-mediated immune response is to an antigen, this data also shows that the subject peptides would also impart tolerance to later challenges to the human of that antigen.

What is claimed is:

1. An isolated peptide of from 6 to 35 amino acids in length comprising an amino acid sequence of formula I:

Ser Pro Xaa$_1$ Gly Xaa$_2$ Cys        I(SEQ ID No. 1)

where Xaa$_1$ is selected from the group consisting of amino acids Tyr, Phe, Trp, and His, and Xaa$_2$ is selected from the group consisting of amino acids Tyr, Phe, Arg, Trp, and His.

2. The peptide of claim 1 which is a lectin derived carbohydrate binding peptide.

3. The peptide of claim 1 which is capable of binding terminally linked α-sialic acid(2→6)βGal- or α-sialic acid (2→3)βGal-groups on structures or molecules comprising such groups.

4. The peptide of claim 1 which suppresses an inflammatory response in a mammal.

5. The peptide of claim 1 which inhibits binding of at least one agent selected from the group consisting of a bacterium, a virus, a bacterial toxin and a viral toxin which binds to terminally linked α-sialic acid(2→6)βGal- or α-sialic acid (2→3)βGal-structures as the agent receptor site on a cell.

6. A pharmaceutical composition comprising a pharmaceutically acceptable carrier and an isolated peptide as defined in claim 1.

7. The pharmaceutical composition of claim 6 which suppresses an inflammatory response in a mammal.

8. The pharmaceutical composition of claim 7, where said inflammatory response arises from antigen challenge in a sensitized mammal.

9. The pharmaceutical composition of claim 8, wherein said inflammatory response is associated with mammalian injury.

10. The pharmaceutical composition of claim 9, wherein said injury is selected from the group consisting of acute respiratory distress syndrome (ARDS), reperfusion injury, frost bite, and septic shock.

11. The pharmaceutical composition of claim 7, wherein said peptide is administered within 1 to 10 hours after initiation of the mammal's immune response but at or prior to one-half the period required for maximal inflammation.

12. The pharmaceutical composition of claim 6 which inhibits binding of at least one agent selected from the group consisting of a bacterium, a virus, a bacterial toxin and a viral toxin which binds to terminally linked α-sialic acid (2→6)βGal- or α-sialic acid(2→3)βGal-structures as the agent receptor site on a cell.

13. The pharmaceutical composition of claim 6 which is administered via a route selected from the group consisting of parenterally, orally, intranasally, intratracheally and transdermally.

14. The pharmaceutical composition of claim 13, wherein said administration is parenteral administration selected from the group consisting of intravenously and intramuscularly.

15. The pharmaceutical composition of claim 6 which provides administration of said peptide at a dosage ranging from about 0.5 to 50 mg/kg body weight.

16. A peptide selected from the group consisting of: Pro Gln Glu Gln Ile Thr Gln His Gly Ser Pro Tyr Gly Arg Cys (amino acids 9–23 of SEQ ID NO: 3), Pro Gln Glu Gln Ile Thr Gln His Gly Ser Pro Tyr Gly Arg Cys-CO—NH$_2$ (amino acids 9–23 of SEQ ID NO: 3), Ser Thr Pro Gly Ile Val Ilc Pro Pro Gln Glu Gln Ile Thr Gln His Gly Ser Pro Tyr Gly Arg Cys (SEQ ID NO: 3), Ser Pro Tyr Gly Arg Cys-CO—NH$_2$ (amino acids 18–23 of SEQ ID NO: 3), Biotin-Ser Pro Tyr Gly Arg Cys-CO—NH$_2$ (amino acids 18–23 of SEQ ID NO: 3), Gly Ala Phe Asp Leu Lys Thr Thr Phe Cys Ile Met Thr Thr Aug Asn Thr Gly Gln Pro Ala (SEQ ID NO: 4), Phe Val Arg Ser Gly Gln Pro Val Ile Gly Ala Cys Thr Ser Pro Tyr Asp Gly Lys Tyr Trp Ser Met Tyr Ser Arg Leu Arg Lys Met Leu Tyr (SEQ ID NO: 5), Pro Lys Ala Leu Phe Thr Gln Gln Gly Gly Ala Tyr Gly Arg Cys (amino acids 9–23 of SEQ ID NO: 6), Arg Leu Leu Ala Ser Thr Asn Ser Arg Leu Cys Ala Val Phe Val Arg Asp Gly (SEQ ID NO 9), and Pro Gln Glu Gln Ile Thr Gln His Gly Ser Gln Tyr Gly Tyr Cys (SEQ ID NO 10).

17. The peptide of claim 16 which is a lectin derived carbohydrate binding peptide.

18. The peptide of claim 16 which is capable of binding terminally linked α-sialic acid(2→6)βGal- or α-sialic acid (2→3)βGal-groups on structures or molecules comprising such groups.

19. The peptide of claim 16 which suppresses an inflammatory response in a mammal.

20. A pharmaceutical composition comprising a pharmaceutically acceptable carrier and an isolated peptide as defined in claim 16.

21. The pharmaceutical composition of claim 20 which suppresses an inflammatory response in a mammal.

22. The pharmaceutical composition of claim 21, where said inflammatory response arises from antigen challenge in a sensitized mammal.

23. The pharmaceutical composition of claim 22, wherein said inflammatory response is associated with mammalian injury.

24. The pharmaceutical composition of claim 23, wherein said injury is selected from the group consisting of acute respiratory distress syndrome (ARDS), reperfusion injury, frost bite, and septic shock.

25. The pharmaceutical composition of claim 21, wherein said peptide is administered within 1 to 10 hours after initiation of the mammal's immune response but at or prior to one-half the period required for maximal inflammation.

26. The pharmaceutical composition of claim 20 which is administered via a route selected from the group consisting of parenterally, orally, intranasally, intratracheally and transdermally.

27. The pharmaceutical composition of claim 26, wherein said administration is parenteral administration selected from the group consisting of intravenously and intramuscularly.

28. The pharmaceutical composition of claim 20 which provides administration of said peptide at a dosage ranging from about 0.5 to 50 mg/kg body weight.

* * * * *

SEQUENCE LISTING (1) GENERAL INFORMATION:

(iii) NUMBER OF SEQUENCES: 12

(2) INFORMATION FOR SEQ ID NO: 1:

```
        (i) SEQUENCE CHARACTERISTICS:
            (A) LENGTH: 6 amino acids
            (B) TYPE: amino acid
            (D) TOPOLOGY: linear (ix) FEATURE:
            (A) NAME/KEY: Modified-site
            (B) LOCATION: 3
            (D) OTHER INFORMATION: /note= "X is selected from the
                group consisting of amino acids Tyr, Phe, Trp and
                His or peptide mimetics thereof"

(ix) FEATURE:
            (A) NAME/KEY: Modified-site
            (B) LOCATION: 5
            (D) OTHER INFORMATION: /note= "X is selected from the
                group consisting of amino acids Tyr, Phe, Arg, Trp
                and His or peptide mimetics thereof"

(xi) SEQUENCE DESCRIPTION: SEQ ID NO: 1:

Ser Pro Xaa Gly Xaa Cys
1               5

(2) INFORMATION FOR SEQ ID NO: 2:

(i) SEQUENCE CHARACTERISTICS:
            (A) LENGTH: 8 amino acids
            (B) TYPE: amino acid
            (D) TOPOLOGY: linear (ix) FEATURE:
            (A) NAME/KEY: Modified-site
            (B) LOCATION: 3
            (D) OTHER INFORMATION: /note= "X is selected from the
                group consisting of amino acids Tyr, Phe, Trp and
                His of peptide mimetics thereof"

(ix) FEATURE:
            (A) NAME/KEY: Modified-site
            (B) LOCATION: 5
            (D) OTHER INFORMATION: /note= "X is selected from the
                group consisting of amino acids Tyr, Phe, Arg,
                Trp, and His or peptide mimetics thereof"

(ix) FEATURE:
            (A) NAME/KEY: Modified-site
            (B) LOCATION: 7
            (D) OTHER INFORMATION: /note= "4-6 amino acids"

(ix) FEATURE:
            (A) NAME/KEY: Modified-site
            (B) LOCATION: 8
            (D) OTHER INFORMATION: /note= "X is selected from the
                group consisting of amino acids Tyr, Phe, Trp and
                His or peptide mimetics thereof"

(xi) SEQUENCE DESCRIPTION: SEQ ID NO: 2:

Ser Pro Xaa Gly Xaa Cys Xaa Xaa
1               5

(2) INFORMATION FOR SEQ ID NO: 3:

(i) SEQUENCE CHARACTERISTICS:
            (A) LENGTH: 23 amino acids
            (B) TYPE: amino acid
            (D) TOPOLOGY: linear (xi) SEQUENCE DESCRIPTION: SEQ ID NO: 3:

Ser Thr Pro Gly Ile Val Ile Pro Pro Gln Glu Gln Ile Thr Gln His
1               5                   10                  15

Gly Ser Pro Tyr Gly Arg Cys
                20
```

(2) INFORMATION FOR SEQ ID NO: 4:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO: 4:

```
Gly Ala Phe Asp Leu Lys Thr Thr Phe Cys Ile Met Thr Thr Arg Asn
1               5                   10                  15
Thr Gly Gln Pro Ala
            20
```

(2) INFORMATION FOR SEQ ID NO: 5:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO: 5:

```
Phe Val Arg Ser Gly Gln Pro Val Ile Gly Ala Cys Thr Ser Pro Tyr
1               5                   10                  15
Asp Gly Lys Tyr Trp Ser Met Tyr Ser Arg Leu Arg Lys Met Leu Tyr
            20                  25                  30
```

(2) INFORMATION FOR SEQ ID NO: 6:

(i) SEQUENCE CHARACTERISTICS:
        (A) LENGTH: 23 amino acids
        (B) TYPE: amino acid
        (D) TOPOLOGY: linear (xi) SEQUENCE DESCRIPTION: SEQ ID NO: 6:

```
Val Ala Pro Gly Ile Val Ile Pro Pro Lys Ala Leu Phe Thr Gln Gln
1               5                   10                  15
Gly Gly Ala Tyr Gly Arg Cys
            20
```

(2) INFORMATION FOR SEQ ID NO: 7:

(i) SEQUENCE CHARACTERISTICS:
        (A) LENGTH: 31 amino acids
        (B) TYPE: amino acid
        (D) TOPOLOGY: linear (xi) SEQUENCE DESCRIPTION: SEQ ID NO: 7:

```
Ala Gly Phe Ile Tyr Arg Glu Thr Phe Cys Ile Thr Thr Ile Tyr Lys
1               5                   10                  15
Thr Gly Gln Pro Ala Ala Asp His Tyr Tyr Ser Lys Val Thr Ala
            20                  25                  30
```

(2) INFORMATION FOR SEQ ID NO: 8:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO: 8:

```
Cys Ala Ser Pro Tyr Glu Gly Arg Tyr Arg Asp Met Tyr Asp Ala Leu
1               5                   10                  15
Arg Arg Leu Leu Tyr
```

-continued (2) INFORMATION FOR SEQ ID NO: 9:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 9:

Arg Leu Leu Ala Ser Thr Asn Ser Arg Leu Cys Ala Val Phe Val Arg
1               5                   10                  15
Asp Gly (2) INFORMATION FOR SEQ ID NO: 10:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 10:

Pro Gln Glu Gln Ile Thr Gln His Gly Ser Gln Tyr Gly Tyr Cys
1               5                   10                  15

(2) INFORMATION FOR SEQ ID NO: 11:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 11:

Ser Gln Tyr Gly Tyr Cys Gly Phe Gly Ala Glu Tyr
1               5                   10

(2) INFORMATION FOR SEQ ID NO: 12:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 12:

Ser Gln Tyr Gly His Cys
1               5